(12) United States Patent
Orlovsky et al.

(10) Patent No.: US 11,978,562 B2
(45) Date of Patent: *May 7, 2024

(54) SYSTEM AND METHOD FOR MONITORING PASSENGERS AND CONTROLLING AN ELEVATOR SYSTEM

(71) Applicant: VAYYAR IMAGING LTD., Yehud (IL)

(72) Inventors: Michael Orlovsky, Hod Ha-Sharon (IL); Ofer Familier, Tel Aviv (IL); Shay Moshe, Petah Tikva (IL); Rotem Barda, Tel Aviv (IL); Ronen Tur, Binyamina (IL); Noga Barpal, Tel Aviv (IL); Albert Jacob, Modiin (IL); Iddo Bar David, Talmei Elazar (IL); Tomer Zimmerman, Tel Aviv (IL)

(*) Notice: Subject to any disclaimer, the term of this patent is extended or adjusted under 35 U.S.C. 154(b) by 51 days.

This patent is subject to a terminal disclaimer.

(21) Appl. No.: 17/625,821

(22) PCT Filed: Dec. 15, 2020

(86) PCT No.: PCT/IB2020/061959
§ 371 (c)(1),
(2) Date: Jun. 6, 2022

(87) PCT Pub. No.: WO2021/124098
PCT Pub. Date: Jun. 24, 2021

(65) Prior Publication Data
US 2022/0293276 A1    Sep. 15, 2022

(51) Int. Cl.
*B66B 1/34* (2006.01)
*A61B 5/00* (2006.01)
(Continued)

(52) U.S. Cl.
CPC .......... *G16H 50/30* (2018.01); *A61B 5/0002* (2013.01); *A61B 5/02055* (2013.01);
(Continued)

(58) Field of Classification Search
CPC ... A61B 5/0002; A61B 5/02055; A61B 5/021; A61B 5/02405; A61B 5/05;
(Continued)

(56) References Cited

U.S. PATENT DOCUMENTS 4,438,831 A * 3/1984 Rohanna ............... B66B 1/3484
187/314
4,970,834 A    11/1990 Polson
(Continued)

FOREIGN PATENT DOCUMENTS

CN    110118966 A    8/2019
CN    110329857 A    10/2019
(Continued)

OTHER PUBLICATIONS

Linda A. Selvey, et al., "Entry Screening for Infectious Diseases", Emerging Infectious Diseases, Feb. 28, 2015, pp. 197-201, vol. 21, No. 2, Centers for Disease Control and Prevention, Atlanta, GA, USA.

*Primary Examiner* — Christopher Uhlir
(74) *Attorney, Agent, or Firm* — AlphaPatent Associates Ltd.; Daniel J. Swirsky

(57) ABSTRACT

Systems and methods for a radar-based viral transmission prevention for a protected space are disclosed. The system comprises a gateway screening system 104 configured for remotely screening subjects crossing a boundary of a protected space, an elevator monitoring system 106 configured for monitoring passengers using an elevator system and a social distance monitoring system 108 configured for monitoring social distancing compliance within the protected space. The system also includes a telemedical monitoring system 110 configured and operable for remotely measuring one or more parameters of a patient using a radar-based system. The system further includes a gesture recognition (Continued)

system 112 configured and operable to identify hand gestures remotely.

9 Claims, 19 Drawing Sheets

(51) Int. Cl.

| | | |
|---|---|---|
| *A61B 5/02* | (2006.01) | |
| *A61B 5/0205* | (2006.01) | |
| *A61B 5/021* | (2006.01) | |
| *A61B 5/024* | (2006.01) | |
| *A61B 5/05* | (2021.01) | |
| *A61B 5/08* | (2006.01) | |
| *A61B 5/11* | (2006.01) | |
| *B66B 5/00* | (2006.01) | |
| *G01S 13/88* | (2006.01) | |
| *G16H 15/00* | (2018.01) | |
| *G16H 40/67* | (2018.01) | |
| *G16H 50/30* | (2018.01) | |
| *G16H 50/80* | (2018.01) | |

(52) U.S. Cl.
CPC .......... *A61B 5/021* (2013.01); *A61B 5/02405* (2013.01); *A61B 5/05* (2013.01); *A61B 5/0816* (2013.01); *A61B 5/112* (2013.01); *A61B 5/4561* (2013.01); *A61B 5/4806* (2013.01); *B66B 1/3423* (2013.01); *B66B 1/3453* (2013.01); *B66B 1/3461* (2013.01); *B66B 1/3476* (2013.01); *B66B 5/0012* (2013.01); *G01S 13/88* (2013.01); *G16H 15/00* (2018.01); *G16H 40/67* (2018.01)

(58) Field of Classification Search
CPC ..... A61B 5/0816; A61B 5/112; A61B 5/4561; A61B 5/4806; B66B 1/28; B66B 1/32; B66B 1/3476; B66B 1/3484; B66B 5/0006; B66B 5/0012; B66B 2201/20; B66B 2201/21; B66B 2201/215; B66B 2201/222; B66B 2201/4676; B66B 2201/4684

See application file for complete search history.

(56) References Cited

U.S. PATENT DOCUMENTS

| | | | |
|---|---|---|---|
| 8,260,042 B2* | 9/2012 | Peng | B66B 5/0012 |
| | | | 382/162 |
| 11,724,909 B2* | 8/2023 | Sudi | B66B 1/2408 |
| | | | 187/247 |
| 2004/0138535 A1 | 7/2004 | Ogilvie | |
| 2007/0222599 A1 | 9/2007 | Coveley et al. | |
| 2010/0191124 A1* | 7/2010 | Prokoski | G16H 30/20 |
| | | | 600/473 |
| 2015/0269873 A1 | 9/2015 | Rowe et al. | |
| 2017/0140587 A1 | 5/2017 | Ambrefe, Jr. et al. | |
| 2019/0047819 A1* | 2/2019 | Vaunois | B66B 5/0012 |
| 2019/0317191 A1* | 10/2019 | Santra | G01S 13/881 |
| 2021/0269280 A1* | 9/2021 | Venkatachalam | H04W 12/72 |
| 2021/0390807 A1* | 12/2021 | Chaurasia | G07C 9/27 |
| 2023/0211978 A1* | 7/2023 | Siman Tov | B66B 1/3476 |
| | | | 187/392 |

FOREIGN PATENT DOCUMENTS

| | | |
|---|---|---|
| JP | 2011212146 A | 10/2011 |
| WO | WO-2021194944 A1 * | 9/2021 |

* cited by examiner

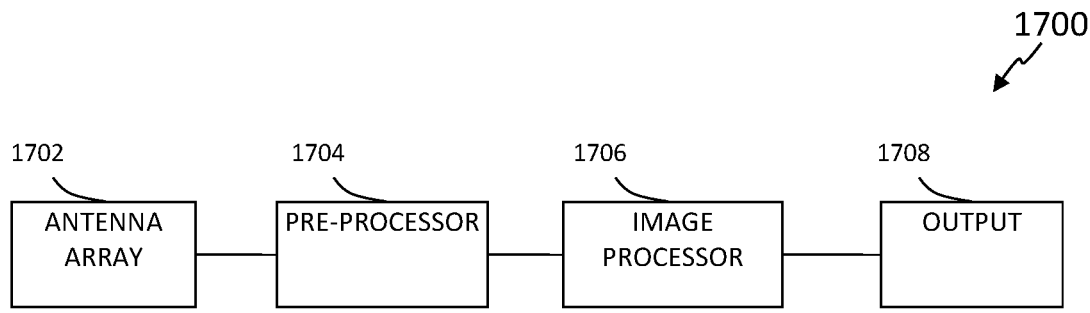
FIG. 17
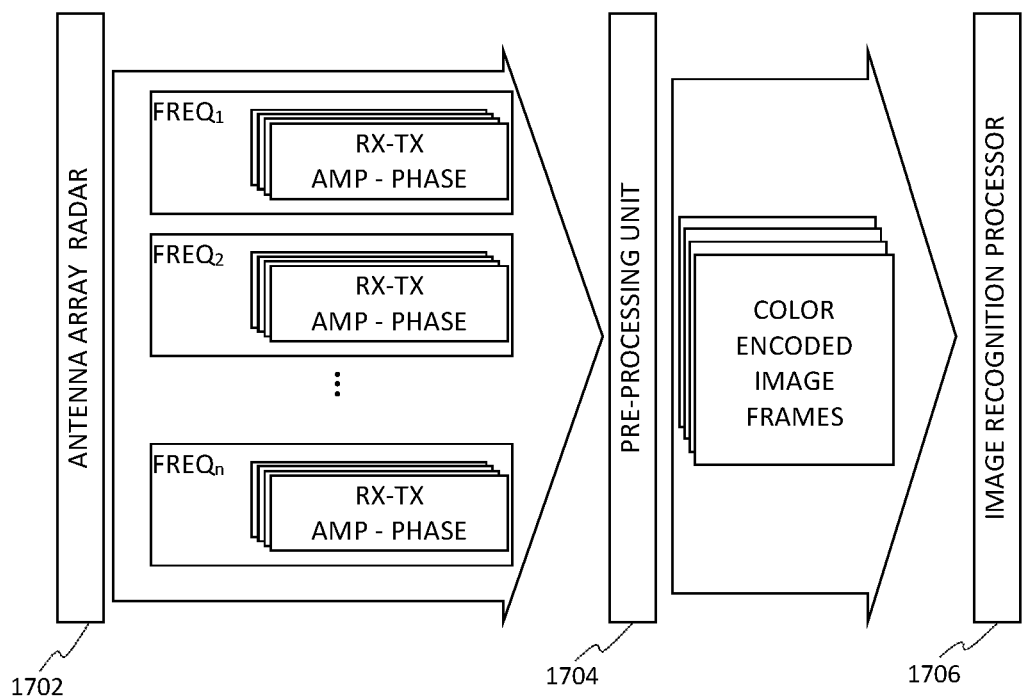
FIG. 18
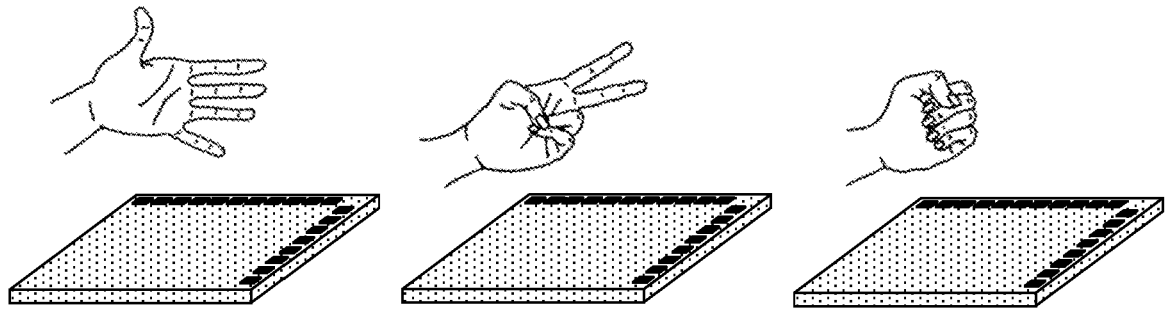
FIG. 19A     FIG. 19B     FIG. 19C

SYSTEM AND METHOD FOR MONITORING PASSENGERS AND CONTROLLING AN ELEVATOR SYSTEM

CROSS-REFERENCE TO RELATED APPLICATIONS

This application is a U.S. National Phase Application under 35 U.S.C. 371 of International Application No. PCT/IB2020/061959, which has an international filing date of Dec. 15, 2020, which claims the benefit of priority from U.S. Provisional Patent Application No. 62/948,830, filed Dec. 17, 2019, U.S. Provisional Patent Application No. 63/042,023, filed Jun. 22, 2020, U.S. Provisional Patent Application No. 63/042,033 filed Jun. 22, 2020, U.S. Provisional Patent Application No. 63/042,037, filed Jun. 22, 2020 and U.S. Provisional Patent Application No. 63/070,835, filed Aug. 27, 2020, the contents of which are incorporated by reference in their entirety.

FIELD OF THE INVENTION

The disclosure herein relates to systems and methods for preventing viral transmission in a protected space. In particular, the disclosure relates to radar enabled prevention of viral transmission in a protected space.

Health workers are at risk of infection when screening potentially infectious patients. Many infections are transferred through physical contact with carriers or through droplets or airborne particles within a short range of the carrier. Nevertheless, it is necessary to perform health screening on subjects that may be carriers of infectious diseases.

Elevator systems include a number of stops and a moving cabin which transits between those stops. The capacity of elevator cabins is limited both by weight and density of passengers however although it is relatively easy for elevators to measure the weight of the load they carry, it remains difficult for elevators to monitor the actual density of passengers within the cabin.

Similarly, it is useful for elevator systems to manage the stopping schedule of the traveling cabin which typically requires a knowledge of the number of passengers waiting at each stop. Although waiting passengers are encouraged to use a manual button to notify the elevator system of their presence, there is no direct method of monitoring the number of passengers waiting by each stop.

Further, for safety purposes, the number of people to be allowed in a hall or conference room is limited. The Corona pandemic is an extreme example of where it is desirable to monitor the number of people in a defined space. People within such a defined space are also expected to maintain a separation between them.

Where there is risk of infection of larger numbers of individuals it is often necessary to prevent a carrier of an infectious disease from entering an area of high population density. Here too it is sometimes necessary to come into contact with carriers of infectious diseases as part of a screening operation.

However, visiting a doctor's clinic or hospital is not always viable for the patient due to certain limitations, especially during extreme situations, like the current Corona pandemic. Moreover, senior citizens especially have difficulty traveling to the doctor' for non-critical problems. Further, in situations where a patient is located away from their preferred doctor and possibly away from their insurance network, e.g., while traveling, locating and receiving affordable healthcare may be difficult. If a patient is seen by a doctor outside of the patient's insurance network, for example, the patient may be responsible for all or at least a larger portion of the medical expenses incurred.

Few health monitoring devices have been developed which measure the physical parameters of the patient and transmit the data to the medical examiner. These devices have attachments which need to be attached to the patient's body for measuring the vital parameters. The provision of attachments disturbs the patient and makes it uncomfortable to undergo the process repeatedly, especially when asleep. Also, these devices cannot monitor certain parameters continuously.

The need remains, therefore, for a method of remotely screening subjects, particularly suspected carriers of infectious diseases. A telehealth solution is needed which can non-intrusively perform physical examination of the patient remotely without visiting the doctor and can provide the examination report to the doctor for treatment advice. The invention described herein addresses the above-described needs.

SUMMARY

The current disclosure addresses various aspects of a viral prevention system for remote screening of subjects and generating appropriate notifications.

According to one aspect of the presently disclosed subject matter, there is provided a viral transmission prevention system for a protected space comprising a gateway screening system for remotely screening subjects crossing a boundary of the protected space, an elevator monitoring system for monitoring passengers using an elevator system and a social distancing monitoring system for monitoring social distancing compliance within the protected space.

As appropriate, the gateway screening system comprising at least one remote health monitor configured and operable to measure at least one health parameter of each subject within a target zone outside the boundary, a processor in communication with the at least one remote health monitor and operable to receive the at least one health parameter and to execute a screening function for determining a boundary-state for each subject and at least one output indicator configured and operable to indicate the boundary-state for each monitored subject.

As appropriate, the boundary-state of CLOSED indicates that the subject is not allowed to not cross the boundary and the boundary-state of OPEN indicates that the subject is allowed to cross the boundary and the screening function is operable to calculate a health index for each subject and to return the boundary-state of OPEN only if the calculated health index is within a permittable range.

As appropriate, the elevator monitoring system comprising at least one cabin-based radar monitor configured and operable to monitor passengers within at least one elevator cabin, at least one waiting zone radar monitor configured and operable to monitor passengers in a waiting zone, a processor configured and operable to receive data from the at least one cabin-based radar monitor, and the at least one waiting zone radar monitor, to analyze the data received from the at least one cabin-based radar monitor and the at least one waiting zone radar monitor and to execute an elevator control function to control the elevator system.

As appropriate, the social distancing monitoring system comprising at least one radar sensor array unit covering an area within the protected space and a processor operable to image objects in the covered area within the protected space, identify people in the covered area, count the number of people in the covered area and determine separation between the people in the covered area within the protected space.

According to another aspect of the presently disclosed subject matter, the viral transmission prevention system further comprises at least one telemedical monitoring system configured and operable to remotely examine the subject by measuring the at least one health parameter.

As appropriate, the telemedical monitoring system comprises a radar-based telemedical monitoring device configured to receive the at least one health parameter of the subject, a data analyzing unit configured to analyze the received health parameter and generate a health profile of the subject and a communicator configured to send the health profile of the subject for examination.

According to another aspect of the presently disclosed subject matter, the viral transmission prevention system also comprises at least one gesture recognition system configured and operable to identify hand gestures remotely.

As appropriate, the gesture recognition system comprises a radar including a linear array of transmitter antennas and a linear array of receiver antennas, wherein the transmitter antennas transmit the electromagnetic waves towards the target zone and the receiver antennas receive the electromagnetic waves reflected back from objects within the target zone, a preprocessing unit comprising a communication unit operable to receive a raw-data package, a memory element operable to store the received data package and a processor operable to execute a data-conversion protocol thereby generating an image data file and an image processor comprising a communication unit operable to receive the image data file and a pattern recognition unit operable to detect patterns within the image data file.

As appropriate, the radar generates the raw-data package comprising an associated phase value and an associated amplitude value for each transmitter-receiver pair of antennas and transmits the raw-data package to the preprocessing unit.

As appropriate, the processor of the preprocessing unit generates the image file by assigning to each transmitter-receiver pair of antennas: at least one spatial coordinate and a set of image data values based upon at least the associated phase value and the associated amplitude value.

As appropriate, the image processor assigns a gesture state to the target zone.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings:

FIG. 17 is a block diagram representing selected elements in a system for gesture recognition using a scanning radar;

FIG. 18 schematically represents data transfer between an antenna array radar, a pre-processing unit and an image processor;

FIGS. 19A-C represent various gestures which may be identified by the gesture recognition unit;

DETAILED DESCRIPTION OF THE EMBODIMENT

Figure 1:
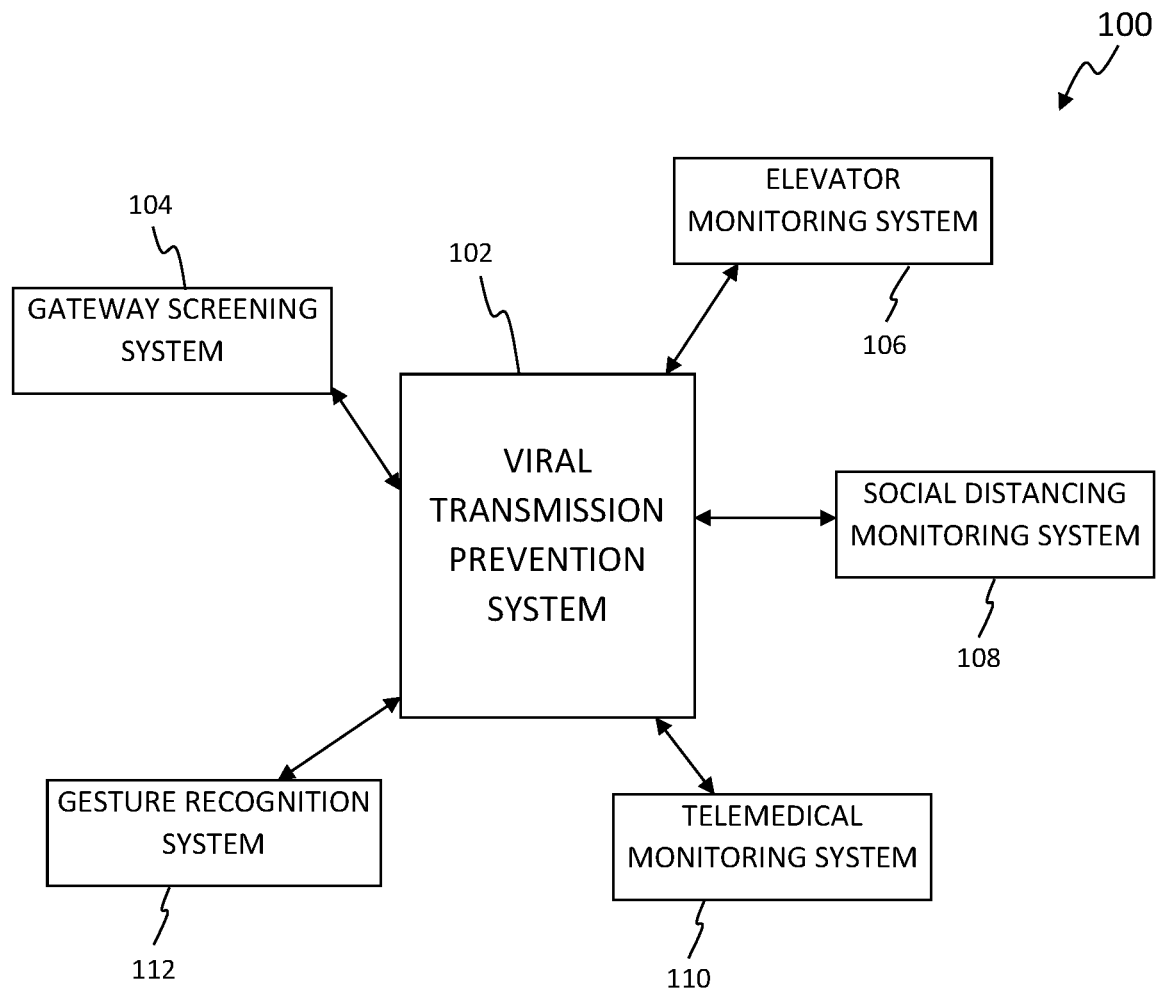
FIG. 1 is a block diagram representing a radar-based system for preventing viral transmission in a protected space.

One or more aspects of the present disclosure relate to systems and methods for remotely health screening subjects crossing a boundary. The system may be used in various applications, In one case, a screening system may be operable to identify subjects presenting particular symptoms, for example indicating an infectious disease, before those subjects enter crowded environments such as schools, hospitals, malls, train stations, public buildings, event halls, parks, fairs, or the like. Additionally or alternatively, it is noted that such systems and methods may be useful for remotely performing preliminary medical testing such as triage or the like.

The system may include a remote health monitor in communication with a processor operable to compute a health status for each subject. Where applicable, a boundary-state may be displayed indicating whether a particular subject has permission to pass a boundary.

In various embodiments, at least one remote health monitor includes a radar system configured and operable to scan the subjects remotely in an anonymous manner and to analyze electromagnetic radiation reflected from the subjects so as to obtain required health parameters.

The other aspects of the present disclosure relate to systems and methods for monitoring and controlling an elevator system. In particular the disclosure relates to using radar-based monitors to monitor the cabins and waiting zones of an elevator system. The monitors generate data relating to the density and the movement of passengers. A central controller uses the generated passenger data to control the elevator system.

In various embodiments, at least one elevator system monitor includes a radar system configured and operable to scan the subjects remotely in an anonymous manner and to analyze electromagnetic radiation reflected from the subjects so as to obtain required parameters.

Yet other aspects of the present disclosure relate to systems and methods for monitoring adherence to social distancing guidelines.

Radar imaging and ultrasonic imaging systems can be implemented using waves with a wavelength in the order of 0.1 cm-10 cm, and typically about 1 cm. Such systems are capable of operating in darkness and can penetrate objects which are not transparent to visible light. The wavelength of 1 cm is sufficient for identifying individuals within an area, but is insufficient to identify them, maintaining their privacy. Radar and Ultrasonic sensors can be used to separately identify individuals despite intervening objects, and are not saturated by natural sources of light and sound.

US Patent Publication 2019/0254544 titled DETECTING AND MEASURING CORRELATED MOVEMENT BY ULTRA-WIDEBAND MIMO RADAR incorporated herein by reference provides an exemplary method for obtaining a 3D complex-image of moving occupants.

The further aspects of the present disclosure relate to systems and methods for remote examination of the patients using a telemedical monitoring device. In particular, the disclosure relates to the use of radar chips for obtaining patient parameters and analyzing the parameters for generating the examination report. The examination report may be sent to a medical professional for diagnosing illness and advising appropriate treatment.

It should be clearly understood that the terms "doctor", "medical practitioner", "medical professional" and "medical examiner" has the same meaning within the context of the present invention and can be used interchangeably to explain the embodiments.

The further aspects of the present disclosure relate to systems and methods for gesture recognition. A scanning radar including a linear array of transmitter antennas and a linear array of receiver antennas may scan a target region and generate raw-data to be passed to a preprocessing unit. The preprocessing unit may process the raw-data to produce an image data file to be passed to an image processor operable to detect patterns within the image data file. Detected patterns may be used to identify a gesture state for the target region. A series of such gesture states over time may indicate a particular gesture.

The purpose of mapping the raw data onto an image data is to take advantage of the vast progress in applying techniques of Deep Learning, Machine Learning, Neural Networks and similar techniques to images and image sequences. These techniques were shown to tackle problems of recognition and classification of objects in images and events in image sequences while coping with variations in scale (distance), orientation, lighting, objects obstructing each other etc.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As appropriate, in various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting. Accordingly, various embodiments may omit, substitute, or add various procedures or components as appropriate. For instance, the methods may be performed in an order different from described, and various steps may be added, omitted or combined. In addition, aspects and components described with respect to certain embodiments may be combined in various other embodiments.

Referring to FIG. 1 a block diagram 100 is presented which illustrates a radar-based viral transmission prevention system 102 in accordance with an embodiment of the invention. The viral transmission prevention system 102 includes a gateway screening system 104 configured for remotely screening subjects crossing a boundary of a protected space, an elevator monitoring system 106 configured for monitoring passengers using an elevator system and a social distance monitoring system 108 configured for monitoring social distancing compliance within the protected space. The viral transmission prevention system 102 also includes a telemedical monitoring system 110 configured and operable for remotely measuring one or more parameters of a patient including heart rate, heart variability, respiratory rate, sleep scores, posture, etc. using a radar-based system. The viral transmission prevention system 102 further includes a gesture recognition system 112 configured and operable to identify hand gestures remotely.

Figure 2:
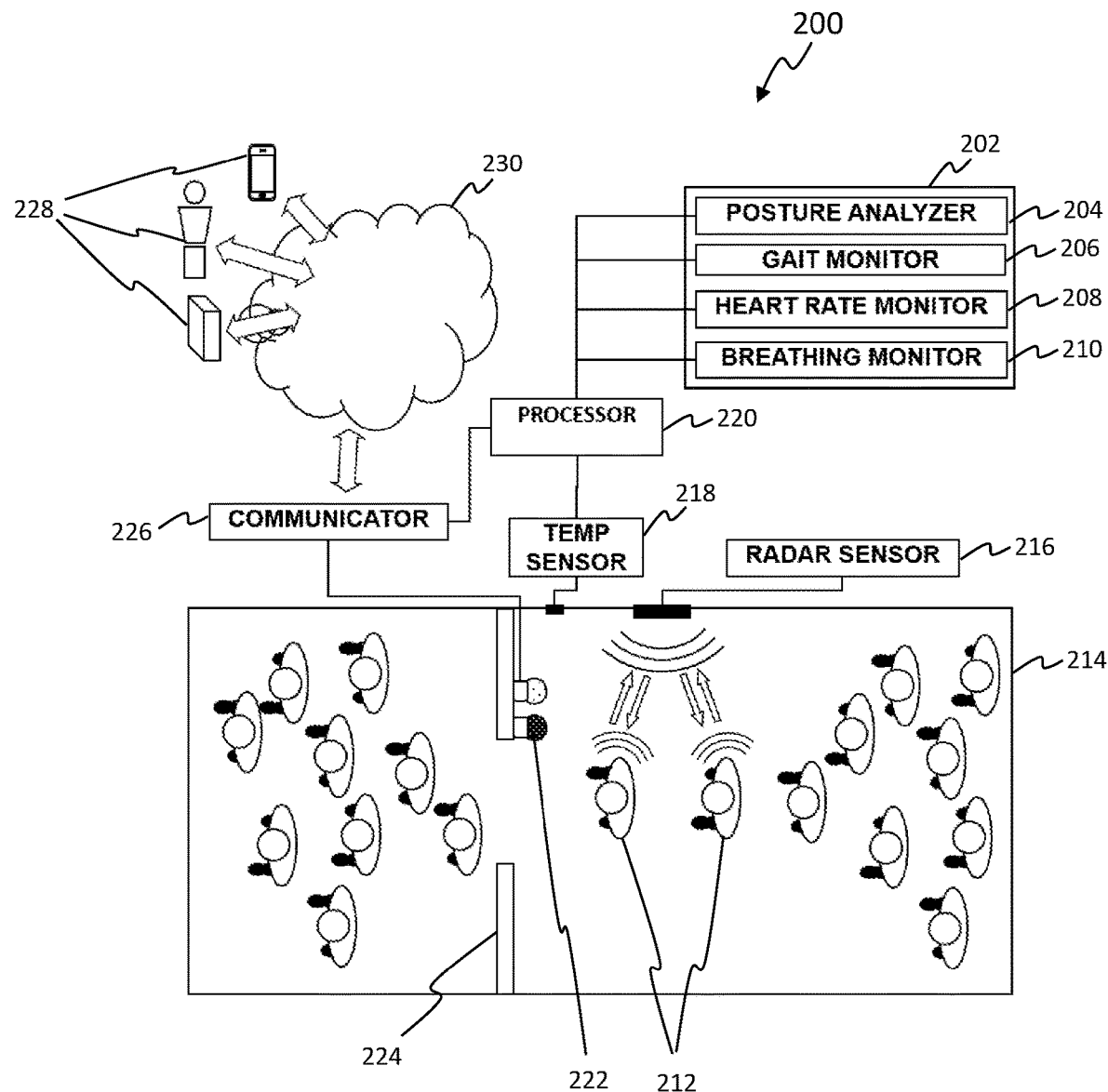
FIG. 2 is a schematic representation of a gateway screening system for remotely screening subjects approaching a boundary threshold.

Reference is now made to FIG. 2 which schematically represents an embodiment of a gateway screening system 200 for remotely screening subjects approaching a boundary threshold. Such a boundary may be a doorway, a gateway, a borderline, an entrance, an exit, a division between an area of high crowd density and an area of low crowd density, and the like as well as combinations of the above.

The system includes at least one remote health monitor 202, at least one processor 220 and at least one output indicator 222.

The remote health monitor is configured and operable to measure at least one health parameter of each subject within a target zone outside the boundary. A variety of health monitors may be provided to compute various health parameters as required. By way of example, a remote heart rate monitor 208 may be provided to determine each subject's heart rate or pulse. Additionally or alternatively, a breathing monitor 210 may be provided to determine each subject's rate of breathing. Still other monitors may include a gait monitor 206 for recording the walking gait of the subjects moving through the target zone, a posture monitor 204 for recording the posture of subjects 212 waiting in the target zone 214.

It is a particular feature of the embodiments described herein that the above mentioned parameters may be monitored using a radar sensor 216 configured and operable to transmit electromagnetic waves towards the target region 214 and to receive electromagnetic waves reflected back from objects 212 within the target region 214. Accordingly, a set of magnitude and phase measurements may be recorded corresponding to the waves scattered back from each voxel within the target zone 214.

Still other health monitors may include a temperature sensor 218 such as an infrared thermometer or the like, a weighing scale, such as an underfloor spring balance or the like.

The processor 220 is in communication with the at least one remote health monitor (204, 206, 208, 210 and 218) and operable to receive the various health parameters from the various monitors and analyzers (204, 206, 208, 210 and 218). The health parameters may be used to execute a screening function for determining a health state and possibly a desired boundary-state for each subject 212.

The output indicator 222 may be in communication with the processor 220 and provided to indicate the boundary-state for each monitored subject 212.

A display device such as a pair of indicator lights of different colors or positions, say red and green for example, may be provided to indicate whether the current boundary-state is CLOSED indicating that the subject 212 should not cross the boundary or the current boundary-state is OPEN indicating that the subject 212 may cross the boundary. Other display means may be used, such as additional indicator lights, computer screens, display boards, transmitted notifications to personal display devices and the like. Accordingly, intermediate boundary states, for example indicating that further testing is required or that a waiting period is required may also be indicated as required. Additionally or alternatively the health parameters of the subject 212 may themselves be displayed via the display device.

In some situations all subjects 212 may have a default boundary-state of closed and the screening function may be operable to calculate a health index for each subject 212 and to return a boundary-state of OPEN only if a calculated health index is within a permittable range.

Where required, the system may additionally include a barrier 224, such as a door, a gate, a lock, a screen or the like, which is configured to physically prevent subjects 212 from crossing the boundary when the boundary state is CLOSED.

It is further noted that a communicator 226 may be provided to communicate with remote agents 228 via a computer network 230 such as the Internet. Accordingly, data harvested by the system, such as health parameters, computed health indicators, boundary states and the like may be communicated to interested parties such as managers, health officials, inspectors and the like.

As and when required, the health profiles and health reports of individual patients 212 are sent to the medical examiner 228 for monitoring and treatment. The health profiles and health reports are sent from a database through a communicator 226 which transmits the information to a medical examiner through a communication network 230. The communication network 230 may include a Bluetooth network, a Wired LAN, a Wireless LAN, a WiFi Network, a Zigbee Network, a Z-Wave Network or an Ethernet Network. The health profiles and health reports may be sent to multiple doctors and other interested parties.

Figure 3:
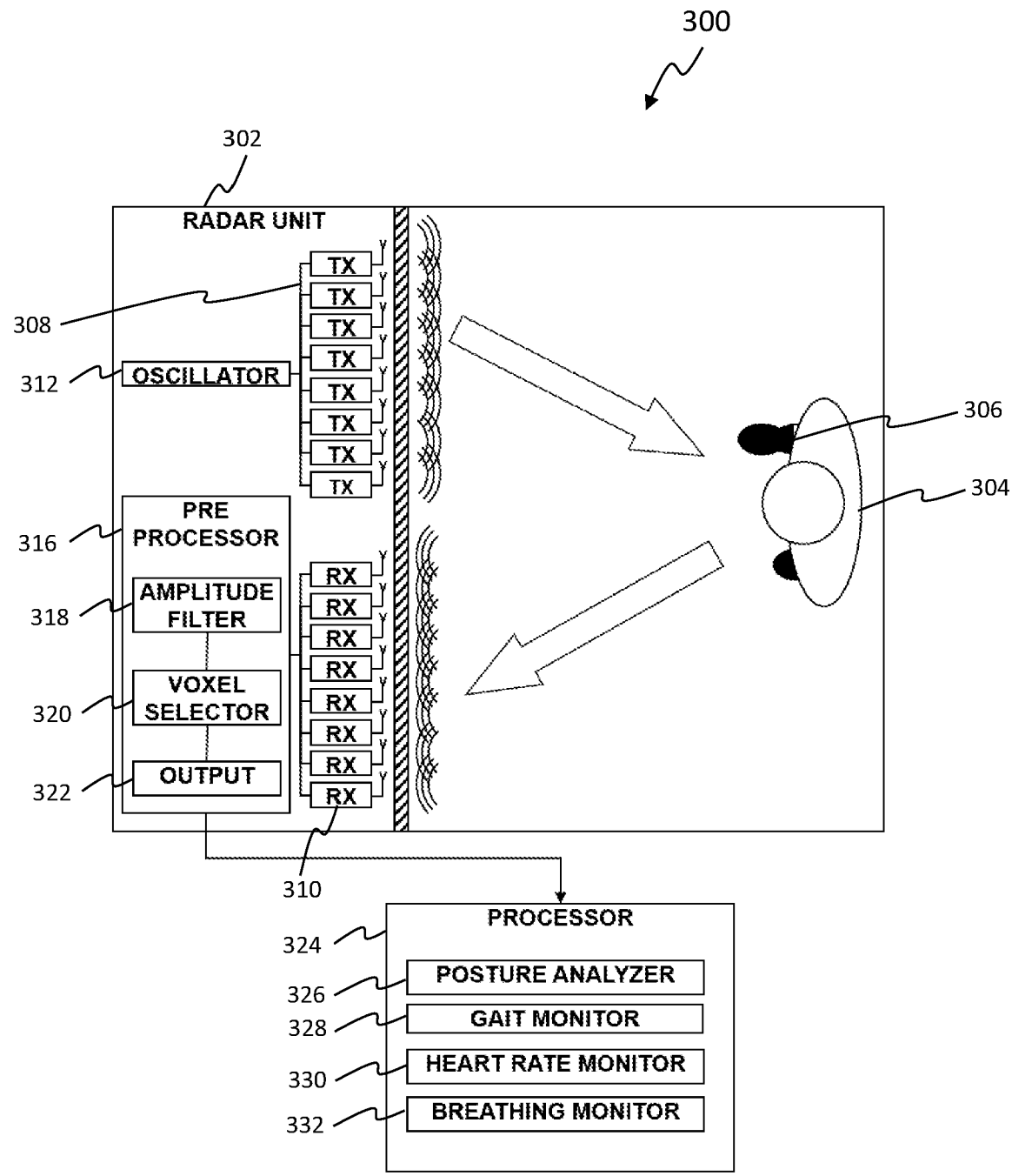
FIG. 3 is a schematic representation of a possible radar system which may be used in the screening system.

Referring now to FIG. 3 which schematically indicates a typical radar system 300 which may be used in the screening system. The radar unit 302 may be mounted to a wall for example, or the like where it may scan a target region 304 in front of the wall. The radar 302 typically includes at least one array of radio frequency transmitter antennas 308 and at least one array of radio frequency receiver antennas 310. The radio frequency transmitter antennas 308 are connected to an oscillator 312 (radio frequency signal source) and are configured and operable to transmit electromagnetic waves towards the target region 304. The radio frequency receiver antennas 310 are configured to receive electromagnetic waves reflected back from objects 306 within the target region 304.

The raw data generated by the receivers 310 is typically a set of magnitude and phase measurements corresponding to the waves scattered back from the objects 306 in front of the array. Spatial reconstruction processing may be applied to the measurements to reconstruct the amplitude (scattering strength) at the three dimensional coordinates of interest within the target region. Thus each three dimensional section of the volume within the target region may be represented by a voxel defined by four values corresponding to an x-coordinate, a y-coordinate, a z-coordinate, and an amplitude value.

Typically, the receivers 310 are connected to a pre-processing unit 316 configured and operable to process the amplitude matrix of raw data generated by the receivers 310 and produce a filtered point cloud suitable for model optimization.

Accordingly, where appropriate, the preprocessing unit may include an amplitude filter 318 operable to select voxels having amplitude above a required threshold and a voxel selector 320 operable to reduce the number of voxels in the filtered data, for example by sampling the data or clustering neighboring voxels.

Figure 4:
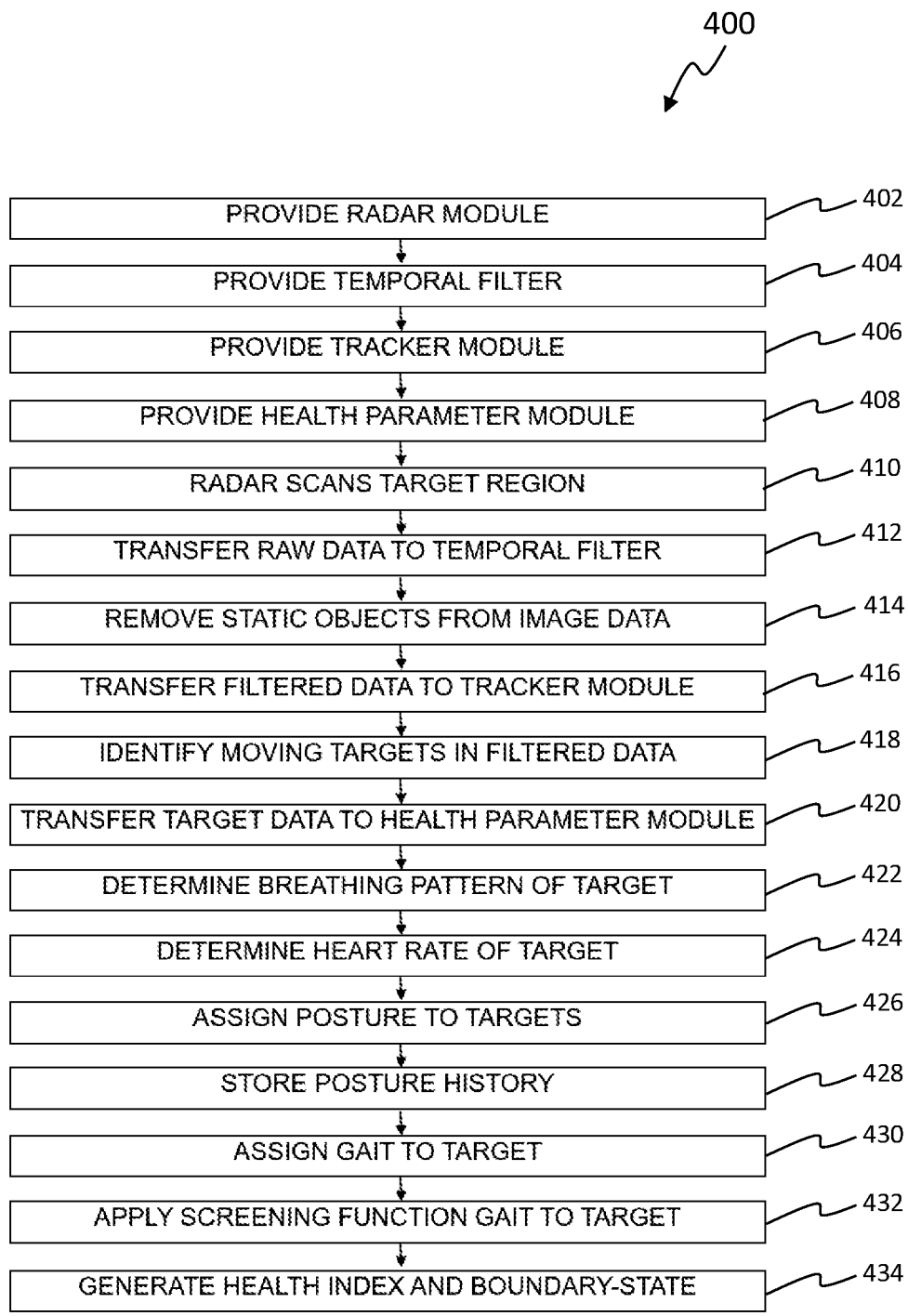
FIG. 4 is a flowchart illustrating actions in a method for generating a heath index and boundary-state associated with a subject.

Referring now to the flowchart 400 of FIG. 4, a method is taught for computing a health index for a target 306 detected in the target region 304 using systems such as described above. The method may include providing a radar unit 302 at step 402 such as described herein, providing at least one processor unit 324 configured to receive raw data from the radar unit 302 and operable to generate a health index based upon the received data and providing a communication module configured and operable to communicate a health index to third parties 228. As required the processor 324 may include a heath parameter module and as required a temporal filter, a tracker such as described in the applicant copending U.S. provisional patent applications Ser. No. 62/952,519 which is incorporated by reference herein.

The method may further include: the radar scanning the target region at step 410, for example by transmitting electromagnetic waves into a monitored region 304 and receiving electromagnetic waves reflected from objects 306 in the monitored region 304; transferring multiple frames of raw data to the pre-processor unit 316 at step 412; removing static objects from the frames of raw data at step 414; transferring filtered data to the tracker module at step 416, identifying moving targets in filtered data at step 418; transferring target data to the health parameter module at step 420; determining breathing pattern for each target at step 422, determining a heart rate for each target at step 424, tracking the moving targets over time and assigning posture to each target at step 426; storing a posture history in a memory unit at step 428; assigning a gait to the target at step 430 and applying a screening function to generate a health index at step 432 and boundary-state for the target at step 434.

It is particularly noted that the filtered data may be analyzed to generate a characteristic displacement signal for each subject which may be indicative of breathing pattern, heart rate, and the like. Various methods for achieving this are described in the applicants U.S. provisional patent applications Ser. Nos. 63/030,943 and 62/297,902 which are incorporated by reference herein.

The method includes identifying at least one displacement pattern within a target region 304 by scanning radiation over the target region 304, the pre-processor unit 316 collating a series of complex values for each voxel representing reflected radiation for the associated voxel in multiple frames; for each voxel determining a center point in the complex plane; determining a phase value for each voxel in each frame; generating a smooth waveform representing phase changes over time for each voxel; selecting a subset of voxels indicative of a pulse pattern; and determining a pulse function for the detected pulse pattern.

The pre-processor 316 may generate a series of frames, where each frame comprises an array of complex values representing radiation reflected from each voxel of the target region 304 during a given time segment.

The method may monitor over a time period a plurality of voxels in parallel. The signal received by the receiver 310 may be given by:

$$s_v[n] = A_v + R_v \cdot \exp\left(j\phi_v + j\frac{4\pi}{\lambda}B_v w[n]\right) + v_v[n]$$

where v is an index of the voxels, n is a time index, $A_v$ is the DC part of the voxel, due to leakage and static objects, $R_v$ is the amplitude (or radius) of the phase varying part of voxel v, $\phi_v$ is a nuisance phase offset of the voxel v, $\lambda$ is the wavelength, $B_v$ is the effective displacement magnitude of the voxel v, $v_v[n]$ is additive noise, and w[n] is the displacement signal waveform at time n.

The time dependent displacement signal w[t] may be isolated from the received signal $s_v[t]$ a selected signal. The displacement signal may then be processed to extract a lower frequency oscillation characteristic of a subject's breathing pattern signal and a higher frequency oscillation characteristic of a subject's heart rate.

Figure 5:
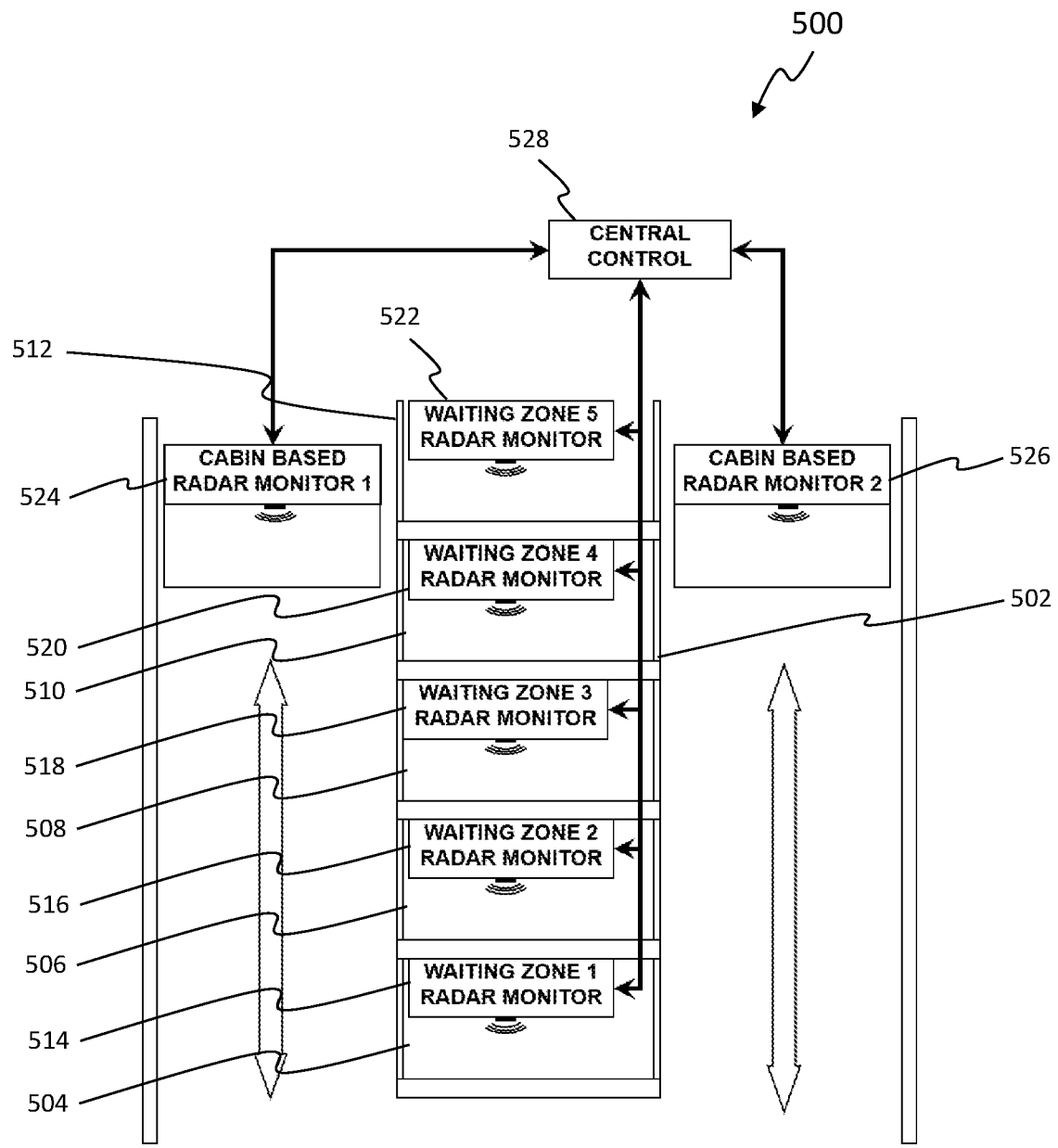
FIG. 5 is a block diagram schematically representing a possible system for monitoring the passengers using an elevator system.

Referring now to FIG. 5 which is a block diagram schematically representing an exemplary system for monitoring the passengers using an elevator monitoring system 500. The elevator monitoring system 500 includes at least one moving cabin 502 which is configured to transit between a number of stops. At each stop there is a waiting zone, waiting zone 1 504, waiting zone 2 506, waiting zone 3 508, waiting zone 4 510 and waiting zone 512 at which passengers generally gather to wait for an available elevator cabin which will carry them to another stop.

The monitoring system 500 of the disclosure includes at least one waiting zone radar monitor. The monitoring system 500 shows five waiting zone radar monitors, waiting zone 1 radar monitor 514, waiting zone 2 radar monitor 516, waiting zone 3 radar monitor 518, waiting zone 4 radar monitor 520 and waiting zone 5 radar monitor 522.

The monitoring system 500 of the disclosure also includes at least one cabin-based radar monitor. A cabin-based radar monitor 1 524 and a cabin-based radar monitor 2 526 are shown in the monitoring system 500. A central controller 528 is also included in the monitoring system 500.

The cabin-based radar monitors 524 and 526 are configured and operable to monitor passengers within at least one elevator cabin 502. The waiting zone radar monitors 514, 516, 518, 520 and 522 are configured and operable to monitor passengers in the waiting zones at the elevator stops 504, 506, 508 510 and 512.

The central controller 528 is in communication with the cabin-based radar monitors 524 and 526 and the waiting zone radar monitors 514, 516, 518, 520 and 522 via data lines. The data lines may be wired communication lines such as telephone lines, Ethernet cables or the like. Additionally or alternatively, the wired or wireless communication networks may serve to connect communication units associated with the monitors and the central control as a network such as a Bluetooth network, a Wired LAN, a Wireless LAN, a WiFi Network, a Zigbee Network, a Z-Wave Network, an Ethernet Network or the like as well as combinations thereof.

Accordingly, the central controller 528 may be configured and operable to receive data from the at least one cabin-based radar monitors 524 and 526 and the at least one waiting zone radar monitors 514, 516, 518, 520 and 522. The central controller 528 may be further operable to analyze the data received from the at least one cabin-based radar monitors 524 and 526 and the at least one waiting zone radar monitors 514, 516, 518, 520 and 522. Accordingly, a processor of the central controller 528 may be operable to execute an elevator control function and thereby to generate control signals which may be communicated via a data communication lines to control the operation of the elevator system 500.

Figure 6:
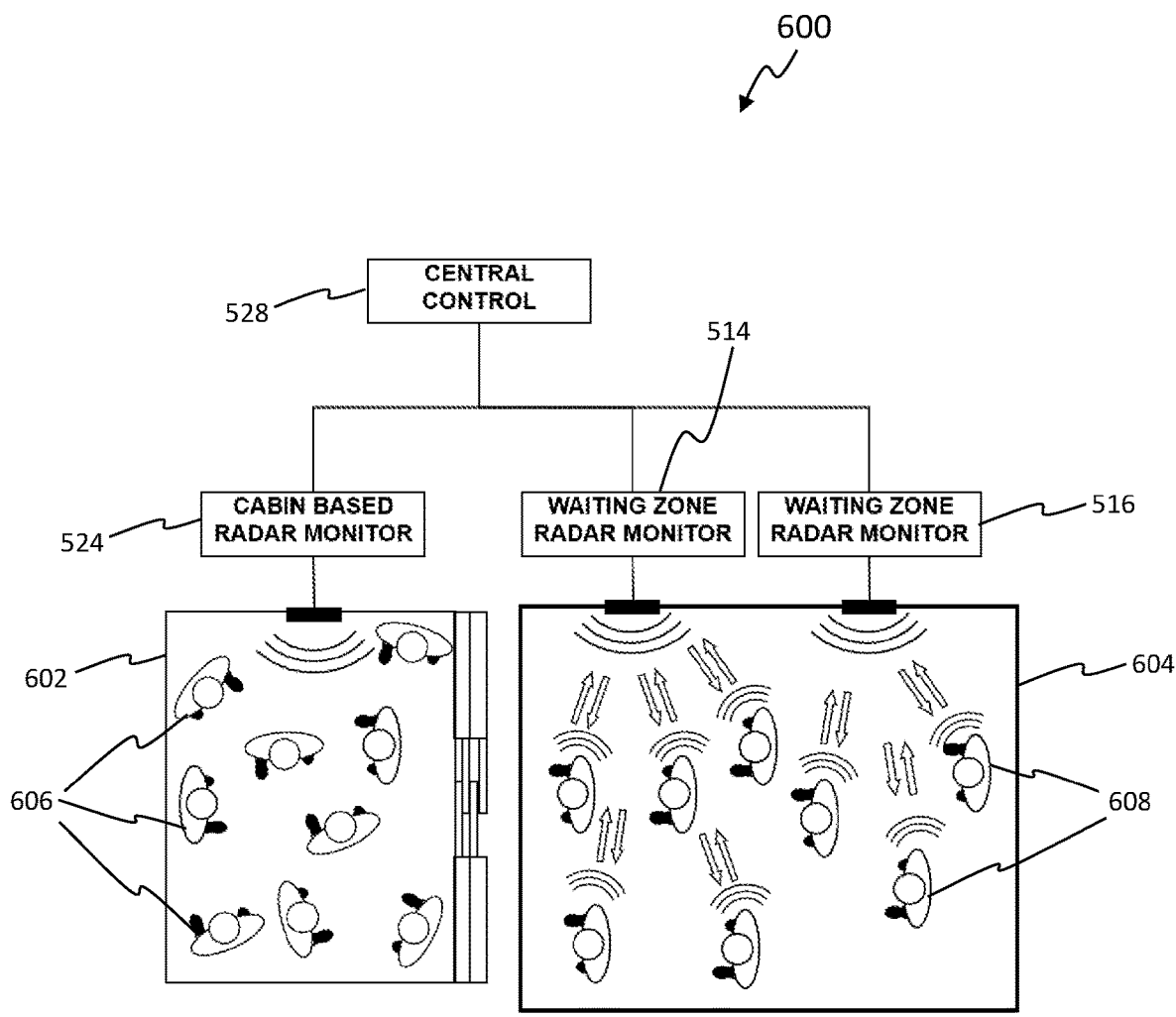
FIG. 6 is a schematic representation of radar-based monitors monitoring passenger density within the elevator cabin and the waiting zone.

Reference is now made to FIG. 6 which schematically represents how radar-based monitors may be used to monitor passenger density within an elevator cabin 602 and within the waiting zone 604.

It is particularly noted that the monitors may be placed in the ceiling or mounted upon a wall or otherwise situated such that passengers do not obscure each other. Where required, for example where the cabin 602 or the waiting zone 604 are large, multiple radar monitored may be used to monitor a common target zone.

Where appropriate radar systems may use radio waves which are selected with a frequency and intensity such that they may pass through obscuring bodies. It is further noted that characteristics of the radio waves may be selected for other required features, for example circularly polarized waves may be used to distinguish between direct and reflected images.

It is further noted that by monitoring the same zone over a period of time, a series of frames may be collected and stored in a memory such that the position and speed of movement of the monitored subjects may be determined. This may be useful for example in the calculation of the timing of closing of the automatic cabin 602 doors to ensure that sufficient time is provided for passengers 606 exiting or entering without causing them injury.

Similarly, the cabin 602 may be prevented from moving if the passenger 606 density is above a required threshold for example where social distancing restrictions limit the proximity permitted between individuals.

Similar restrictions may be imposed upon the people 608 in gathered in the waiting zone 604, for example, guests gathered in a party hall. An alert in the form of an audio/visual alarm may be generated in case the people 608 density is above a required threshold for example where social distancing restrictions limit the proximity permitted between individuals.

Figure 7:
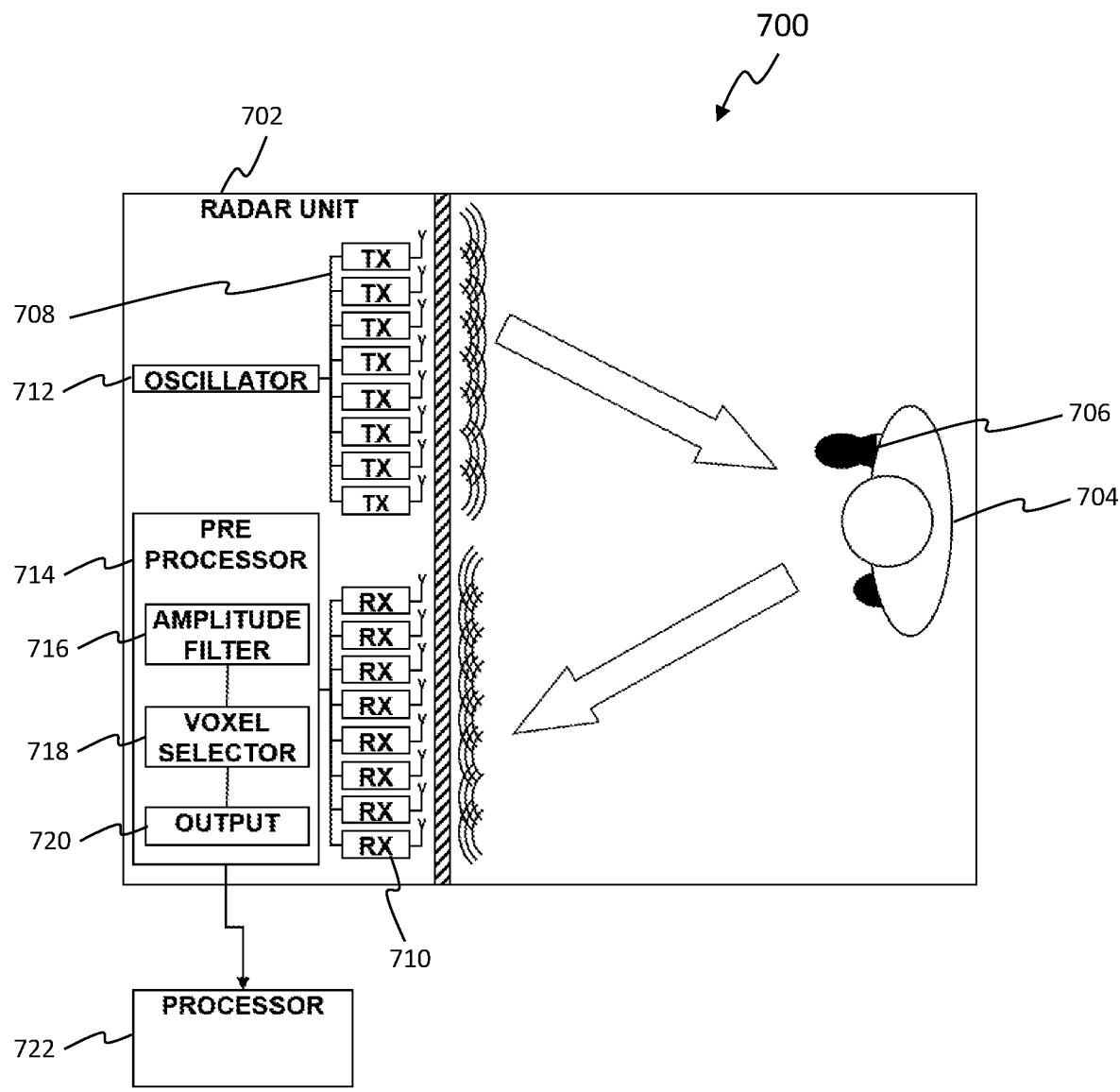
FIG. 7 is a schematic representation of a radar-based monitor unit.

With reference now to FIG. 7, a schematic representation is presented of an example of the radar-based monitor unit 700 which may be used with the passenger monitor system 500.

The typical radar system 702 which may be used in the passenger monitor system 500 may be mounted to a wall for example, or the like where it may scan a target region in front of the wall. The radar 702 typically includes at least one array of radio frequency transmitter antennas 708 and at least one array of radio frequency receiver antennas 710. The radio frequency transmitter antennas 708 are connected to an oscillator 712 (radio frequency signal source) and are configured and operable to transmit electromagnetic waves towards the target region 704. The radio frequency receiver antennas 710 are configured to receive electromagnetic waves reflected back from objects 706 within the target region 704.

Accordingly, the transmitter 708 may be configured to produce a beam of electromagnetic radiation, such as microwave radiation or the like, directed towards a monitored region 704 such as an enclosed room or the like. The receiver 710 may include at least one receiving antenna or array of receiver antennas configured and operable to receive electromagnetic waves reflected by objects 706 within the monitored region 704.

The raw data generated by the receivers is typically a set of magnitude and phase measurements corresponding to the waves scattered back from the objects 706 in front of the array. Spatial reconstruction processing may be applied to the measurements to reconstruct the amplitude (scattering strength) at the three-dimensional coordinates of interest within the target region 704. Thus, each three-dimensional section of the volume within the target region 704 may be represented by a voxel defined by four values corresponding to an x-coordinate, a y-coordinate, a z-coordinate, and an amplitude value.

Typically, the receivers 710 are connected to a pre-processing unit 714 configured and operable to process the amplitude matrix of raw data generated by the receivers 710 and to produce a filtered point cloud suitable for model optimization.

Accordingly, where appropriate, the pre-processing unit 714 may include an amplitude filter 716 operable to select voxels having amplitudes above a required threshold and a voxel selector 718 operable to reduce the number of voxels in the filtered data, for example by sampling the data or clustering neighboring voxels.

Figure 8:
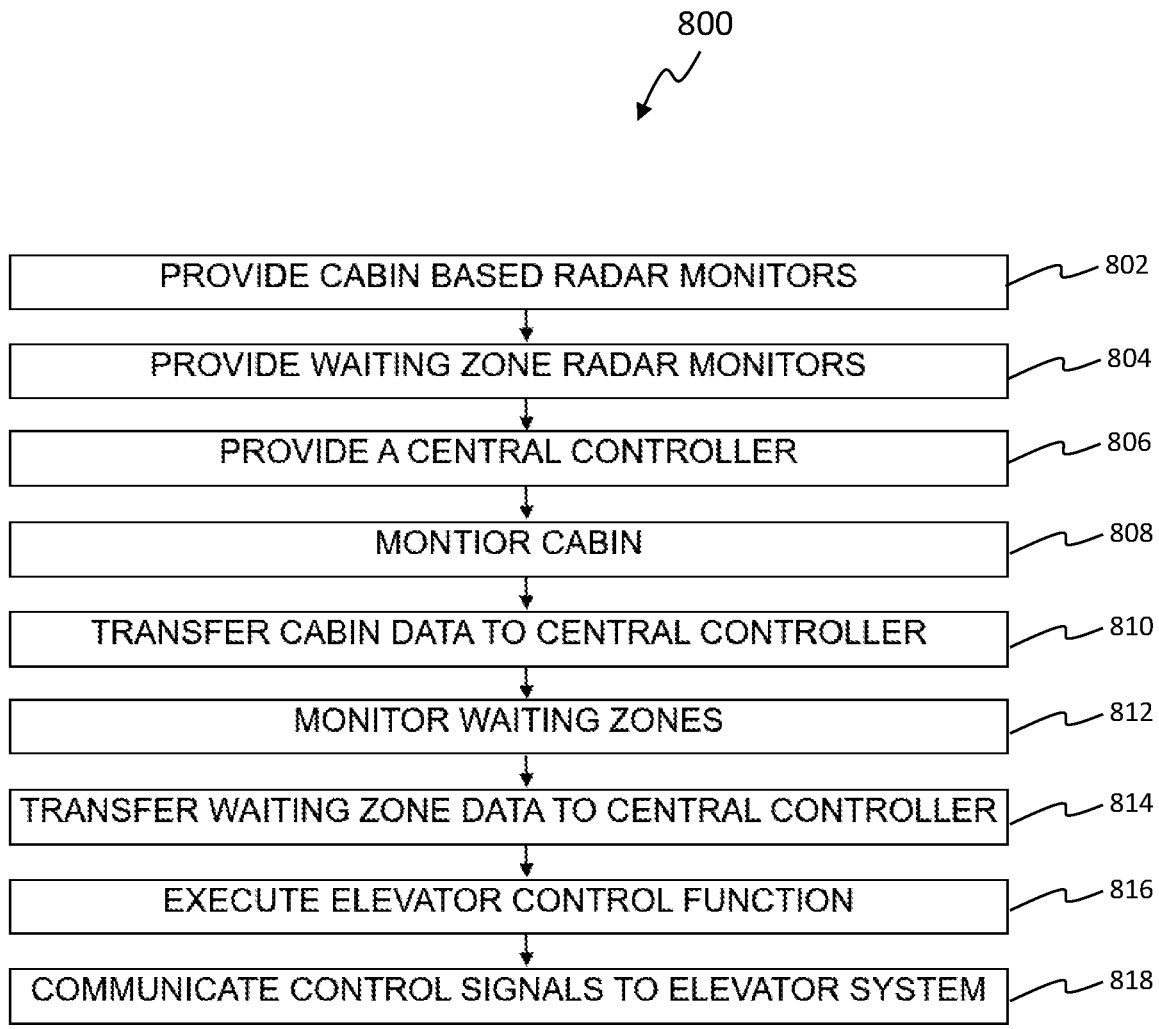
FIG. 8 is a flowchart illustrating actions in a method for controlling an elevator system using data generated by the radar-based monitoring system.

Referring now to the flowchart of FIG. 8, exemplary actions are indicated of a method for controlling an elevator system using data generated by the radar-based passenger monitor system 500.

The method may include providing a monitoring system 500 by installing or otherwise providing cabin-based radar monitors, for example, the cabin-based radar monitor 524 within the elevator cabin 602 at step 802 and installing waiting zone radar monitors 514 and 516 in the waiting zone 604 at the stops of the elevator system at step 804. The method further provides a central controller 528 in communication with the monitors 514, 516 and 524, at step 806.

Accordingly, at step 808, the cabin-based monitor 524 may monitor passenger 606 distribution within the cabin 602 which may be communicated to the central controller 528 at step 810 for providing a passenger cabin distribution metric.

Similarly, the waiting zone monitors 514 and 516 may monitor passenger 608 distribution at each of the elevator stops at step 812 which may be communicated to the central controller 528 at step 814 for providing a passenger waiting distribution metric for each stop.

At step 816, the central controller 528 may use the cabin distribution metric and the passenger waiting distribution metrics received from the monitors 514, 516 and 524 as arguments in the execution of an elevator control function.

At step 808, the elevator control function may thereby select control signals to instruct the elevator to operate as required. For example, controlling the stop schedule of the elevator or controlling the operation of the cabin 606 and stop doors.

For example, the elevator control function may be operable to prevent movement of the elevator cabin 606 if the received data indicates that cabin passenger density is above a threshold value. Additionally or alternatively, the elevator control function may be operable to prevent the elevator doors closing if the received data indicates that cabin 606 passenger density is above a threshold value.

Where appropriate, the elevator control function may be operable to prevent the elevator doors closing if the received data indicates that a passenger is approaching the cabin 606.

In other examples the monitoring system 500 may further include a security scanner configured to generate security passes for passengers. Such a system may be able to prevent tailgating in which an unauthorized individual may gain access to a restricted area by waiting for an authorized individual to open an accessway and then to enter alongside the authorized individual.

Accordingly, the elevator control function may be operable to prevent the elevator doors closing if the received data indicates that there are more passengers within the cabin than the number of security passes provided. In this way tailgating individuals may be prevented from using the elevator. Alternatively, an alert may be provided to security guards such that the unauthorized intruder may be apprehended at the next stop of the elevator. The alert may be provided in audio/visual form.

In some examples, in addition to the passenger density monitor, a health monitor may be provided which is configured and operable to measure at least one health parameter of each passenger within a target zone. As shown in FIG. 2, the health processor 202 may include at least one data analysis agent selected from a group consisting of: a heart rate monitor 208, a breathing monitor 210, a posture analyzer 204, a gait monitor 206, a temperature monitor 218 and the like as well as combinations thereof.

Various examples of heart rate monitors and breathing monitors may be used in the system such as described in the applicants copending United States provisional patent application serial number U.S. Ser. No. 63/030,943 which is incorporated herein by reference in its entirety. Such monitors may be operable to analyze a set of magnitude and phase measurements corresponding to the waves scattered back from the objects in front of a radar sensor to determine vital signs of the subjects such as heart rate and breathing rate.

It is noted that this data may be combined with parameters recorded by other monitors such as temperature sensors and weight monitors. For example, remote temperature sensors may be directed towards the passenger entering the cabin and the weight of the elevator may be monitored as each passenger enters or exits so as to determine the weight of each passenger. Accordingly, it is noted that multiple health parameters may be recorded for each passenger traveling within the elevator cabin.

Figure 9:
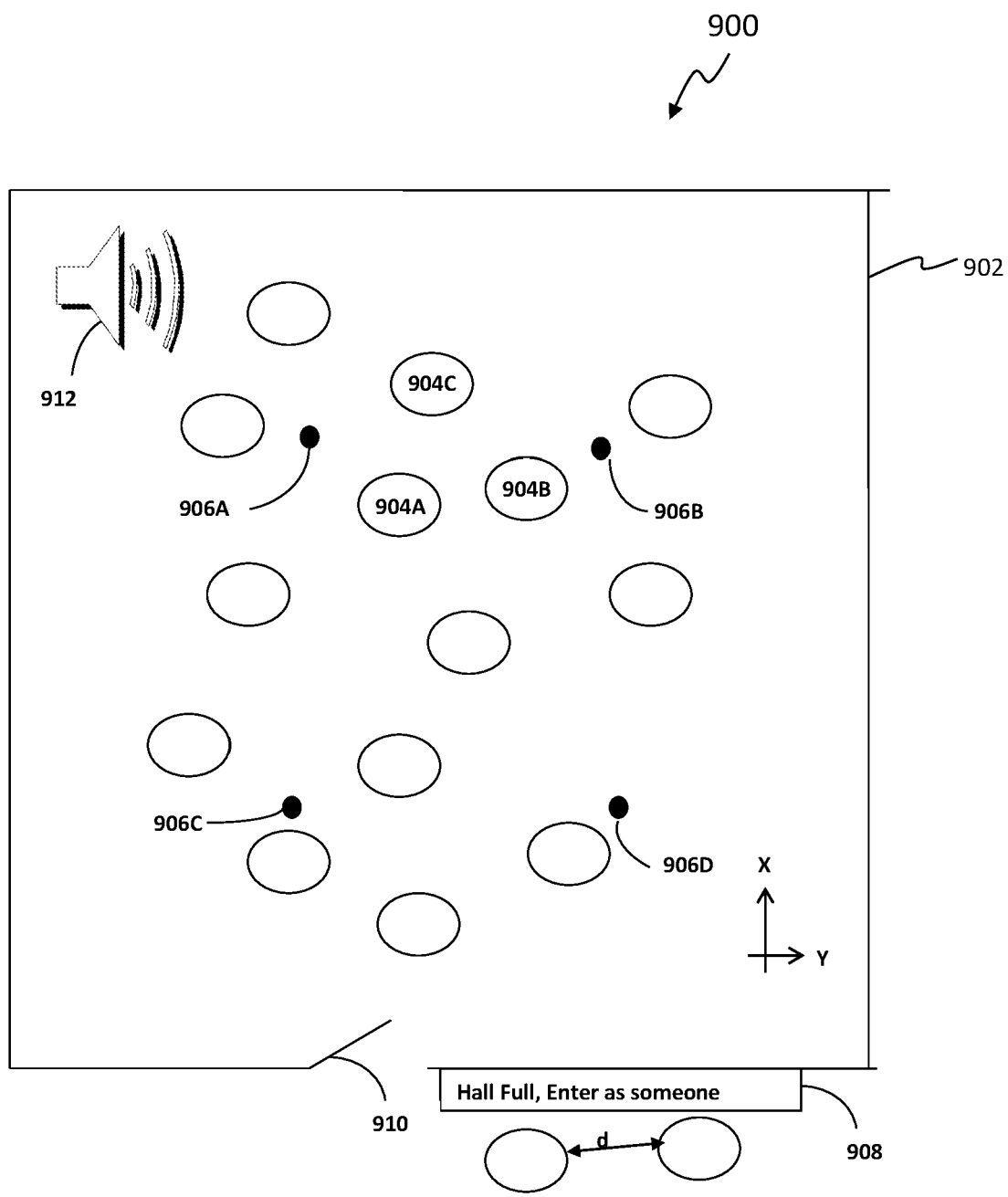
FIG. 9 is a schematic bird's eye view of a hall showing position of people within that hall and position of an array of radar sensors.

Reference is now made to FIG. 9 showing a bird's eye view of a hall 902 showing the position of people 904A, 904B ... within that hall and the position of an array of radar sensors 906A-906D.

The array of radar sensor units 906A-906D enables the continuous monitoring of people 904A, 904B, 904C within a room or hall 902. In a particular embodiment, depending on the size of the hall 902, there is a maximum number of people 5 that may safely be found within the hall. The number of radar sensors units required to monitor a hall depends on the size of the hall, and this can vary from a single sensor unit to a plurality of units depending on the size of the hall. A sign 908 at an entrance 910 can warn that the hall 902 has the maximum number of people allowed therein.

Knowing the size of the room, or indeed the distance between any two points, it is possible to calibrate distances, and a circle of half the diameter of the social separation distance may be drawn around each individual.

The social separation is the required distance between the closest parts of two people. The line joining the centers of two clusters determined as indicating two people, should be at least the social separation distance between the signals indicating the closest elements. If the separation between individuals is less than this distance, or continues for more than a set period, such as a few seconds, an announcement may be triggered from a loudspeaker 912 that people are standing too close. It should be clearly understood that any other audio/visual means can be employed for alerting people for violating social distancing norms.

The image of the hall 902 and people 904A, 904B, 904C ... in it may be displayed remotely to managers of a venue or to the emergency services so that appropriate action may be taken.

There are, of course, other ways of monitoring the number of people in an area, such as with optical security cameras and image analysis, or by monitoring the number of smartphones. Using radar sensors is preferable since privacy is preserved. Also, sometimes a single person carries more than one smartphone, or no smartphone and smartphones may also be switched off. Radar is a preferred solution as it penetrates through obstructions and does not require a line of sight.

Thus, it is particularly noted that it is a feature of the current disclosure that the system may monitor individuals in a passive manner without requiring the monitored individuals to carry any transmitting beacon such as a wearable device, a mobile telephone, a near field communication module or the like. The currently disclosed system is operable to monitor subjects within a target region passively, for example by recording radiation reflected back from the subjects to a receiver.

A preferred embodiment uses a radar sensor array that is integrated together with a digital signal processor (DSP) and a memory into a chip.

One embodiment uses at least one radar sensor array that is integrated together with a digital signal processor (DSP) and a memory into a chip. One such radar unit uses a 4D imaging MIMO radar chip 10A having global frequency bands (60 Ghz or 79 GHz), thousands of virtual channels, a wide field of view on both axis and high resolution—angular and distance. The radar is provided on a chip (ROC) and preferred embodiments cover a dual-band range, supporting both 60 GHz and 79 GHz bands.

Another embodiment operates in the 60-81 GHz frequency bands and has 24 transmitters and 24 receivers.

Another embodiment uses a sensor array that creates high-resolution images in real time based on advanced RF technology with radar bands from 3 GHz-81 GHz having 72 transmitters and 72 receivers integrated with a high-performance DSP with a large internal memory that is capable of executing complex imaging algorithms without needing an external CPU.

Due to the integration of a large number of transceivers and by sending, receiving and analyzing a multitude of signals with advanced DSP, high-resolution 4D images that track contours with high accuracy are obtained.

Figure 10:
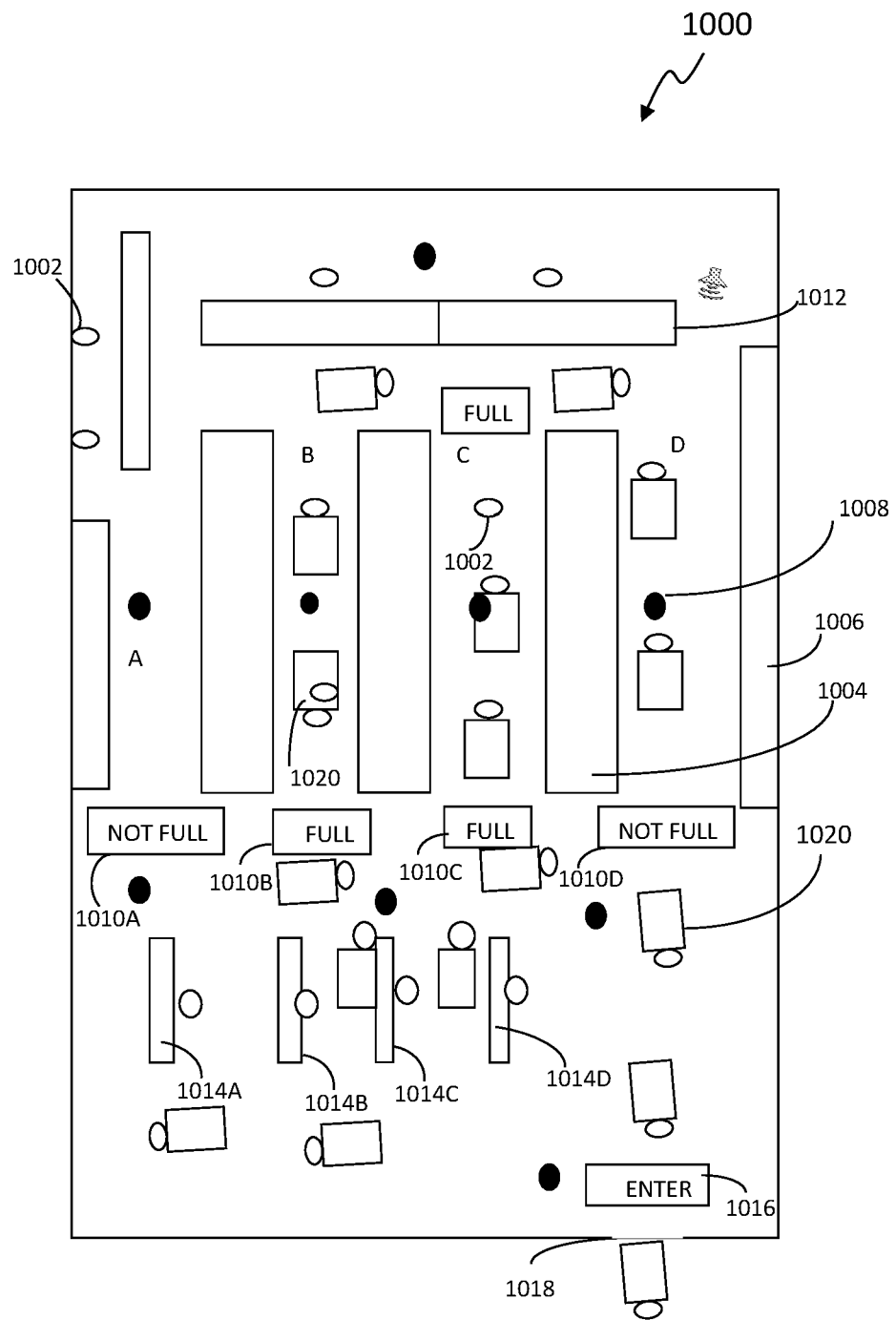
FIG. 10 is a schematic bird's eye view of a supermarket showing position of people within that supermarket, and the position of an array of radar sensors and of indicator lights.

FIG. 10 is a schematic bird's eye view of a supermarket 1000 showing the position of people 1002 within that supermarket 1000, stacks of produce 1004 and shelves 1006, an array of radar sensors 1008 and indicators 1010A, 1010B, 1010C and 1010D, counters 1012 and checkout positions 1014A, 1014B, 1014C and 1014D. The radar sensors 1008 may be positioned for monitoring individual areas such as aisles A, B, C, D, or checkout areas 1014.

Radar 1008 enables the determination of three-dimensional objects over time. By collecting three-dimensional data images over time and subtracting the signals from objects that do not move, the shelves 1006, checkouts 1014A, 1014B, 1014C and 1014D, and stacks 1004 can be removed from the detected reflected signals. This enables the sensor array to identify moving objects which may be trolleys with people 1020 or people 1002 without trolleys, such as staff manning counters 1012 and checkouts 1014A, 1014B, 1014C and 1014D.

In accordance with the permitted number of people allowed in a particular supermarket, a sign 1016 at the entrance 1018 may display an appropriate message, such as WAIT or ENTER, for example. Instead of words, the sign 1016 may simply be a color, for example a green light indicating that it is safe to proceed and a red light indicating that one should wait. Alternatively, a walking pedestrian or a standing pedestrian may be displayed. The layout of the shelving 1016 and stacks 1014 divides the store into areas such as aisles A, B, C, D. At the ends of each such area, a sign 1010D may display a written message such as NOT FULL or PROCEED, or a sign 1010C may display the word FULL or WAIT. Arrows or the symbols of the highway-code may be used to indicate the direction to move, responsive to determinations by the arrays of radar sensors 1008 indicating that an area is full or not. Radar systems 1008 are sensitive enough to determine a trolley 1020 carrying an infant and to count the infant separately from the person pushing the trolley 1020. In such a scenario, or if an adult and a child enter the store 1000 together and keep close together, the system may determine them as as two individuals, but not alert that they are too close together, assuming that they are related. Similarly, by nature of the checkout counters 1014A, 1014B, 1014C and 1014D, the worker and the customer may be closer together than generally permitted, but the worker may be provided with adequate protection.

Nevertheless, waiting trolleys 1020 may be indicated by signs to proceed to a specific checkout counter 1014A, 1014B, as they are vacant.

Thus, supermarkets and the like may be equipped with radar systems that monitor the number of people per area and indicate if it is safe to enter specific areas. They may also monitor the total number of people within and indicate if it is safe to enter, or if one should wait for someone to exit. This may eliminate the need for a doorman or may make the job of a doorman easier.

Similar systems may be employed in shopping malls, post offices, government offices, conference rooms and stores of all types.

Figure 11:
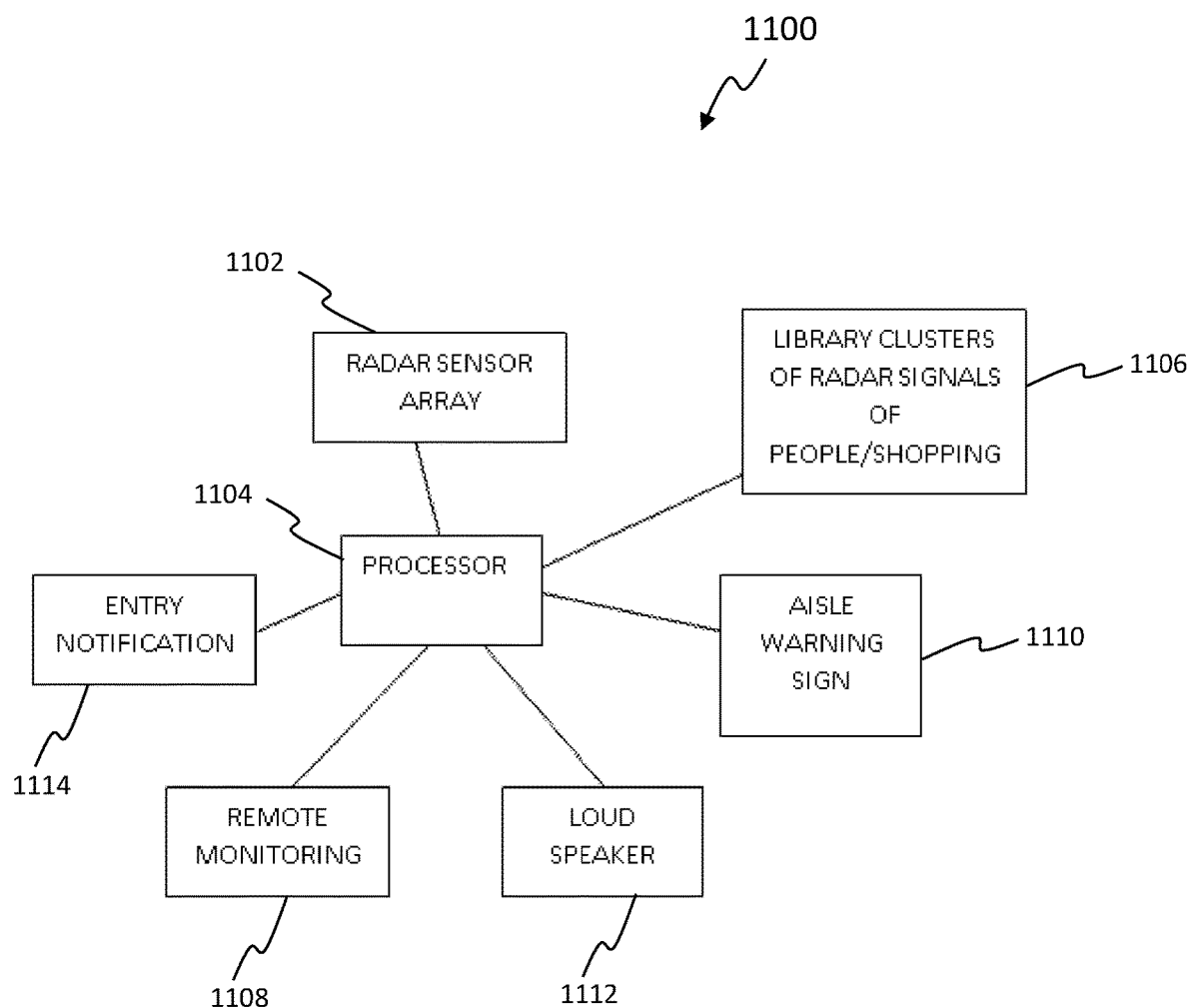
FIG. 11 is a schematic block diagram of a system for monitoring adherence to social distancing threshold guidelines and providing alerts where the density of consumers is too high.

FIG. 11 is a schematic block diagram of a system 1100 for monitoring adherence to social distancing threshold guidelines and providing alerts where the density of people in a supermarket is too high. The system 1100 comprises an array of one or more radar sensor units 1102 that send out radar signals and determine radar reflections. These are processed by a processor 1104 which determines people by removing the background, and then clustering the signals into groups that may be compared with library clusters 1106 to identify as people or processed by tracking movements over time 1108, then provides output in the form of signs 1110, which may simply be lights, standard images such as road-signs and icons that are easily understood, routing arrows or words such as stop, proceed, wait, etc. Audible messages may be provided by a speaker system 1112. An entry notification 1114 at the entrance to the store will let people know if they can or cannot enter. Alternatively, automatic entrance doors may be overridden to prevent entry if the store is full.

The radar sensor array may be one or more integrated systems such as a radar array on a chip with an internal processor, however some tasks as described herein may be performed by an external data processor, such as a computing platform or a distributed computing system. Optionally, the data processor includes or accesses a volatile memory for storing instructions, data, a library of signals indicative of a person, or the like.

Additionally or alternatively, the data processor may access a non-volatile storage, for example, a magnetic hard disk, flash-drive, removable media or the like, for storing instructions and/or data.

In general, the radar sensor units are not required to be high resolution to provide adequate data. They merely need to be able to differentiate between reflections from different individuals by clustering signals together and appropriate processing. Each sensor array unit preferably has a wide field of view and the number of radar sensor arrays required depends on the size and shape of the area being monitored, so that the entire area of the supermarket 10 is covered.

Movement indicating an individual may be macro movement of someone walking around, or the periodicity of movement that indicates breath or heartbeat.

Figure 12:
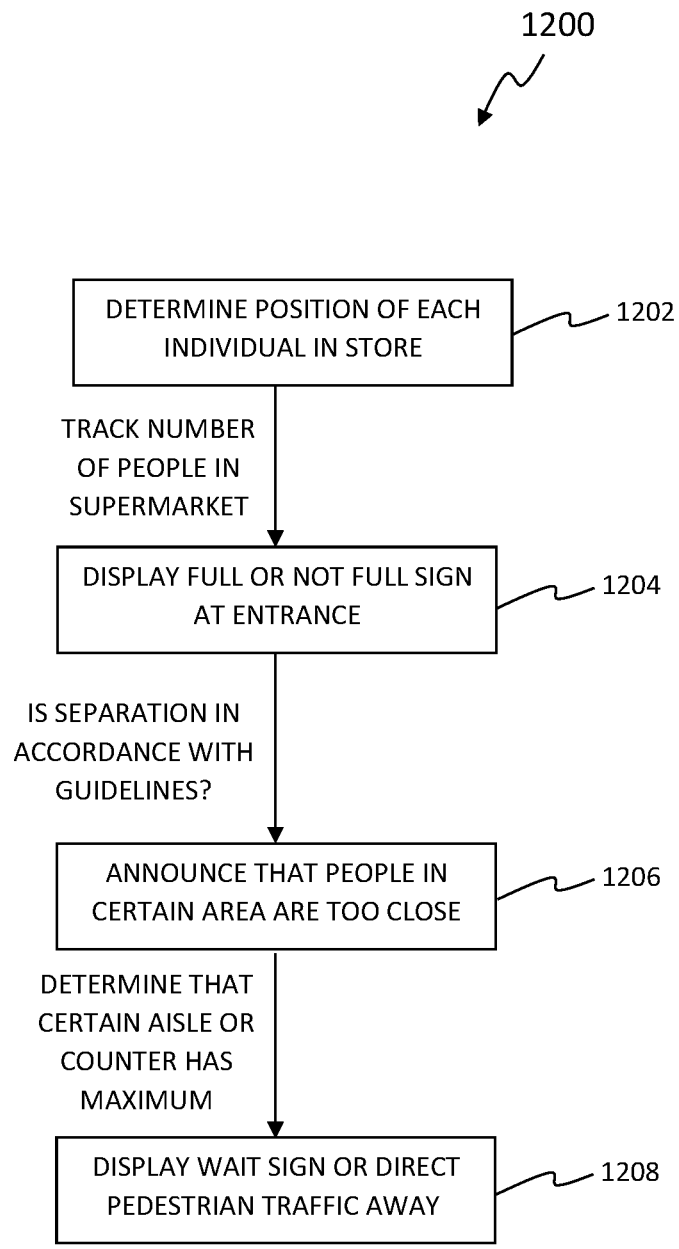
FIG. 12 is a flowchart of a method for monitoring adherence to social distancing guidelines and providing alerts where these guidelines are not being followed.

FIG. 12 is a flowchart 1200 of a method for monitoring adherence to social distancing guidelines and providing alerts where these guidelines are not being followed.

At step 1202, the method requires monitoring the number of people in an area and indicating that it is safe to enter the area or not. The method tracks the number of people in the area or supermarket and displays a "FULL" or "NOT FULL" sign at the entrance of the area at step 1204. The method also monitors separation of individuals and warns if they are too close at step 1206. Depending upon the count of the people in the area through an aisle or a counter, a "wait sign" may be displayed to the pedestrian to wait outside the area till the count is reduced or the outside pedestrian are allowed inside the area or the supermarket.

Thus, a social distancing monitor is provided that comprises radar sensors to monitor the proximity of individuals and provides alerts if social distancing rules are broken. It may be used to monitor queues in retail stores, ticket counters, elevator lines, supermarket aisles etc. and to ensure that a minimum distance between people is maintained.

The social distance monitor may provide automatic routing for supermarkets, malls and the like. The social distance monitor may be configured to count the number of people in a room and to provide an alert if the people count is higher than an allowed threshold based on social distancing guidelines either by a pre-defined maximum count for the room, or by measuring the room size and calculating the maximum count. The system identifies crowded public areas by monitoring the congestion level and alerts if the congestion is higher than pre-defined threshold based on guidelines. The guidelines may be social distancing guidelines. However, even in times where there are no social distancing requirements, there is a need to ensure that the number of people in a room is within safe limits as determined by emergency services, based on size, number of exits and so on.

Figure 13:
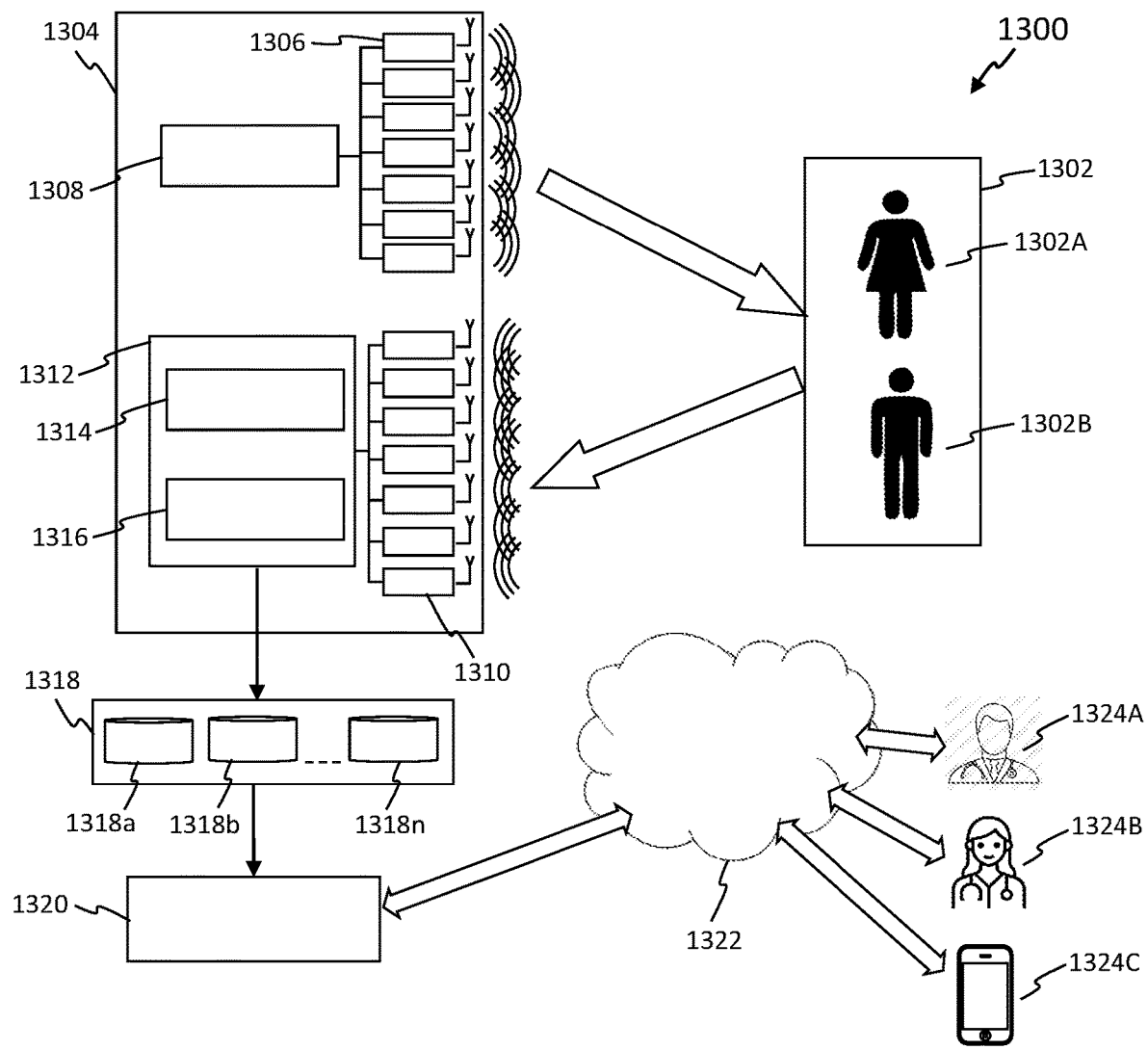
FIG. 13 is a schematic representation of a system for remote examination of patients using radar based telemedical monitoring device.

Reference is now made to FIG. 13, which is a schematic representation of a system 1300 for remote examination of patients. The system 1300 includes a radar-based telemedical monitoring device 1304, a database 1318 and a communicator 1320.

The radar-based telemedical monitoring device 1304 includes an array of transmitters 1306 and an array of receivers 1310. The array of transmitters 1306 may include an oscillator 1308 connected to at least one transmitter antenna or an array of transmitter antennas 1306. Accordingly, the transmitters 1306 may be configured to produce a beam of electromagnetic radiations, such as microwave radiation or the like, directed towards a monitored region 1302 such as an enclosed room, a particular arear of the hospital room, or the like. The receiver 1310 may include an array of receiver antennas configured and operable to receive electromagnetic waves reflected by objects within the monitored region 1302. The monitored region 1302 is shown to include two patients 1302A and 1302B. However, monitored region 1302 may include a smaller area focusing on one patient or a larger area focusing on a large number of patients for measuring the physical parameters without limiting the scope of the invention.

In a particular embodiment, the telemedical monitoring device 1304 monitors the patients 1302A and 1302B without any physical contact or attachments. The telemedical monitoring device 1304 may be appropriately positioned at a distance of a few feet from the monitored region 1302 to effectively monitor the patients 1302A and 1302B. In one embodiment, the telemedical monitoring device 1304 is positioned at the head/foot of a bed or proximate to a chair (not shown) on which the subject 1302A is resting. The telemedical monitoring device 1304 may also be positioned on a table or wall adjacent or opposite the bed (not shown), or on the ceiling of the room to monitor the patients 1302A and 1302B. In a room of a large number of patients, the telemedical monitoring device 1304 may be placed at a center position to capture information from all the patients.

The information received by the receiver 1310 of the telemedical monitoring device 1304 includes various physical parameters of the patients 1302A and 1302B along with patients' profiles. The physical parameters which may be monitored by the telemedical monitoring device 1304 include, but are not limited to, the heart rate, heart variability, respiratory rate, sleep scores, gait, postures, etc. The patient profile includes various information of the patient including, but not limited to, name, age, gender, residence address, profession, dietary information, medical history, current treatment, etc.

The electromagnetic signals received by the receiver 1310 is sent to a processing unit 1312 of the telemedical monitoring device 1304. The processing unit 1312 comprises a subject identifying unit 1314 which filters out the non-desired signals received from other objects present in the monitored region 1302, such as a table, chair, bed, etc. the process of filtering out the non-desired signals is beyond the scope of the present invention. The subject identifying unit 1314 also distinctly identifies the signals received from different subject patients. For example, subject identifying unit 1314 distinctly identifies the signals received from patients 1302A and 1302B and transfers the data to a data analyzing unit 1316 for further processing. The data analyzing unit 1316 analyzes the signals for various monitored parameters, including but not limited to, the heart rate, heart variability, respiratory rate, sleep scores, posture, gait, etc. The data analyzing unit 1316 may prepare separate health profiles for the patients 1302A and 1302B including the monitored parameters. The data analyzing unit 1316 may also prepare health reports for patients, including but not limited to, an inspection report, a palpation report, a percussion report, an auscultation report and a neurologic examination report.

The health profiles and health reports of patients are stored in the database 1318. The health profiles and health reports 1318*a* . . . 1318*n* of each patient are stored individually in the database 1318.

As and when required, the health profiles and health reports of individual patients are sent to the medical examiner for monitoring and treatment. The health profiles and health reports are sent from the database 1318 through a communicator 1320 which transmits the information to a medical examiner 1324A through a communication network 1322. The communication network 1322 may include a Bluetooth network, a Wired LAN, a Wireless LAN, a WiFi Network, a Zigbee Network, a Z-Wave Network or an Ethernet Network. The health profiles and health reports may be sent to multiple doctors 1324*a*, 1324*b*, etc. who are involved in the treatment. The health profiles and health reports may also be sent to a communication device 1324*c* of a caretaker of the patient.

Figure 14:
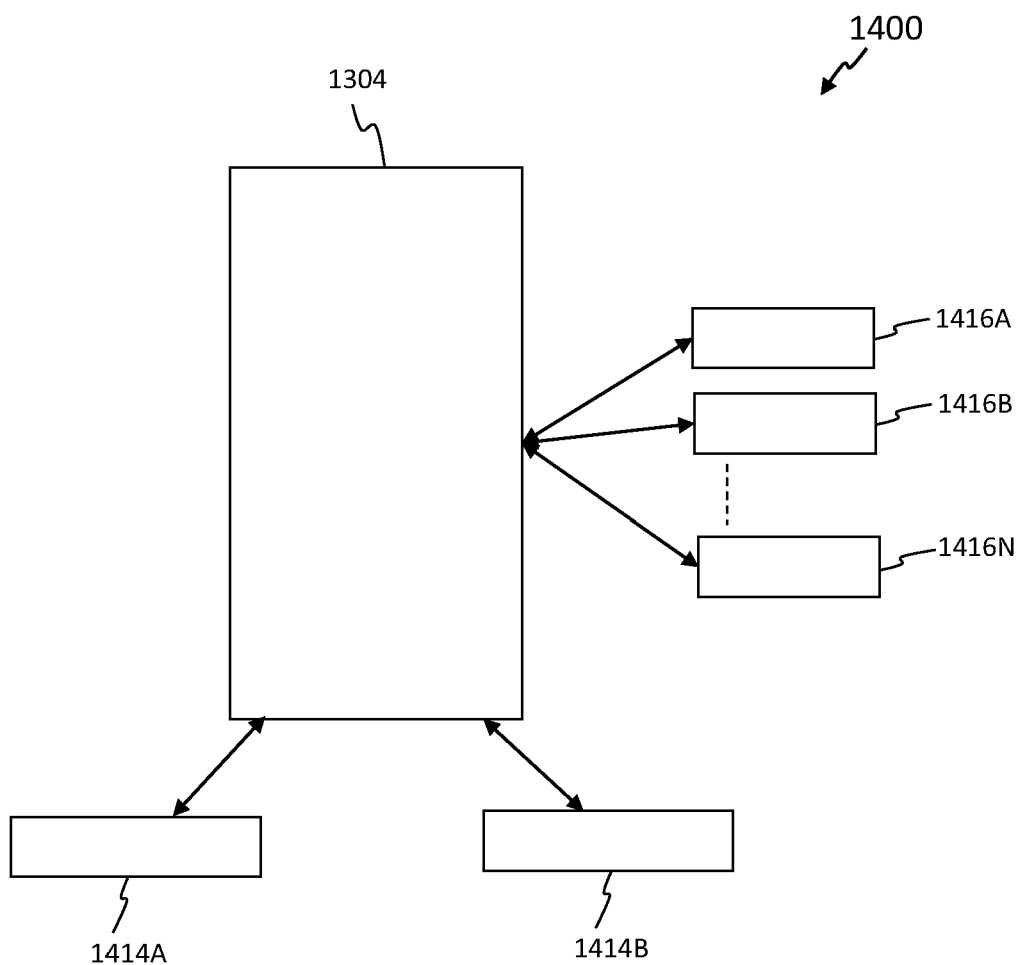
FIG. 14 illustrates a schematic representation of the telemedical monitoring device 104 with attached external units according to an aspect of the invention.

FIG. 14 illustrates a schematic representation of the telemedical monitoring device 1304 with attached external units. In a particular embodiment, the telemedical monitoring device 1304 may connect to various other medical devices for measuring the patient's 1302A and 1302B parameters. The telemedical monitoring device 1304 is shown here connected to a weight measuring unit 1414A and a blood pressure monitoring unit 1414B. The units 1414A and 1414B measure the weight and blood pressure of the patient 1302A and 1302B and transfer the data to the telemedical monitoring device 1304. The telemedical monitoring device 1304 may also connect to a number of sensors 1416A . . . 1416N, like, an acoustic sensor, an infrared body temperature sensor, and other sensors that measure parameters such as ambient humidity, temperature and light level. The integrated data may be used to assess a health condition of the patients 1302A and 1302B. The weight measuring unit 1414A, the blood pressure monitoring unit 1414B and sensors 1416A . . . 1416N may be connected to the telemedical monitoring device 1304 via a Bluetooth connection, a Wired LAN connection, a Wireless LAN connection, a WiFi connection, a Zigbee connection, a Z-Wave connection or an Ethernet Network connection. The telemedical monitoring device 1304 is disclosed here connected to two external measuring units, however, it may connect to any other medical device without limiting the scope of the invention. Exemplary medical devices include, but are not limited to, a pulse oximeter monitoring unit, etc.

Figure 15:
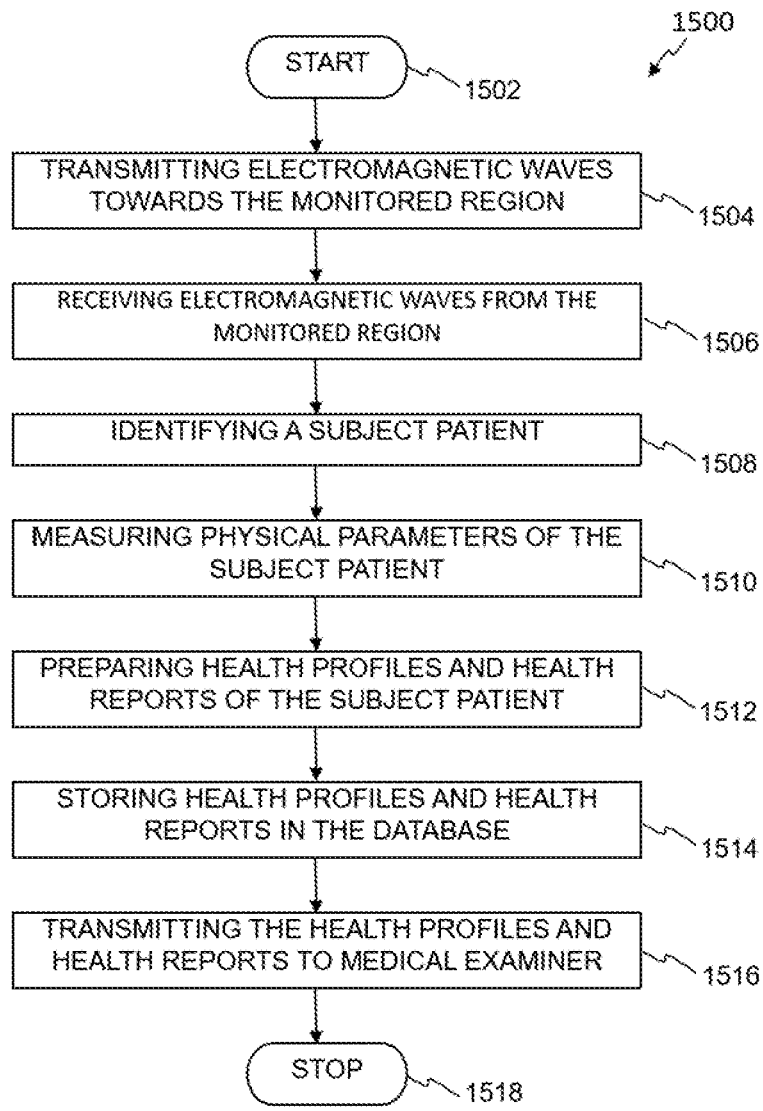
FIG. 15 is a schematic flowchart illustrating an exemplary method for remote examination of the patient according to an aspect of the invention.

Referring to FIG. 15 which is a schematic flowchart illustrating an exemplary method for remote examination of the patient according to an aspect of the invention. The process starts at step 1502 and electromagnetic waves (EM) are transmitted by the transmitter 1306 of the telemedical monitoring device 1304 towards the monitored region 1302 at step 1504. The EM waves reflected from the monitored region 1302 are received by the receiver 1310 at step 1506. The received EM signals are transferred to the subject identifying unit 1314 of the processing unit 1312. At step 1508, the subject identifying unit 1314 filters out the non-desired data and identifies the data of the desired subject. As required, the subject identifying unit 1314 may select the data of one subject patient, e.g. patient 1302A or multiple subject patients, e.g. patients 1302A and 1302B. At step 1510, the data analyzing unit 1316 measures the physical parameters of the subject patient 1302A and prepares health profiles and health records of the patient 1302A at step 1512. The health profiles and health records of the patient 1302A are stored in the database 1318 at step 1514. As and when required, at step 1516, the health profiles and health records of the patient 1302A are sent to one or more of the medical practitioners 1324A and 1324B to assess the medical condition of the patient 1302A and suggest appropriate treatment. The health profiles and health records of the patient 1302A may also be sent to the communication device 1324C of the caretaker of the patient 1302A. The process is completed at step 1518.

The systems and methods explained above may perform physical examination of the patient remotely and non-intrusively. The examination report of the patient may be sent to the doctor for treatment advice.

Figure 16:
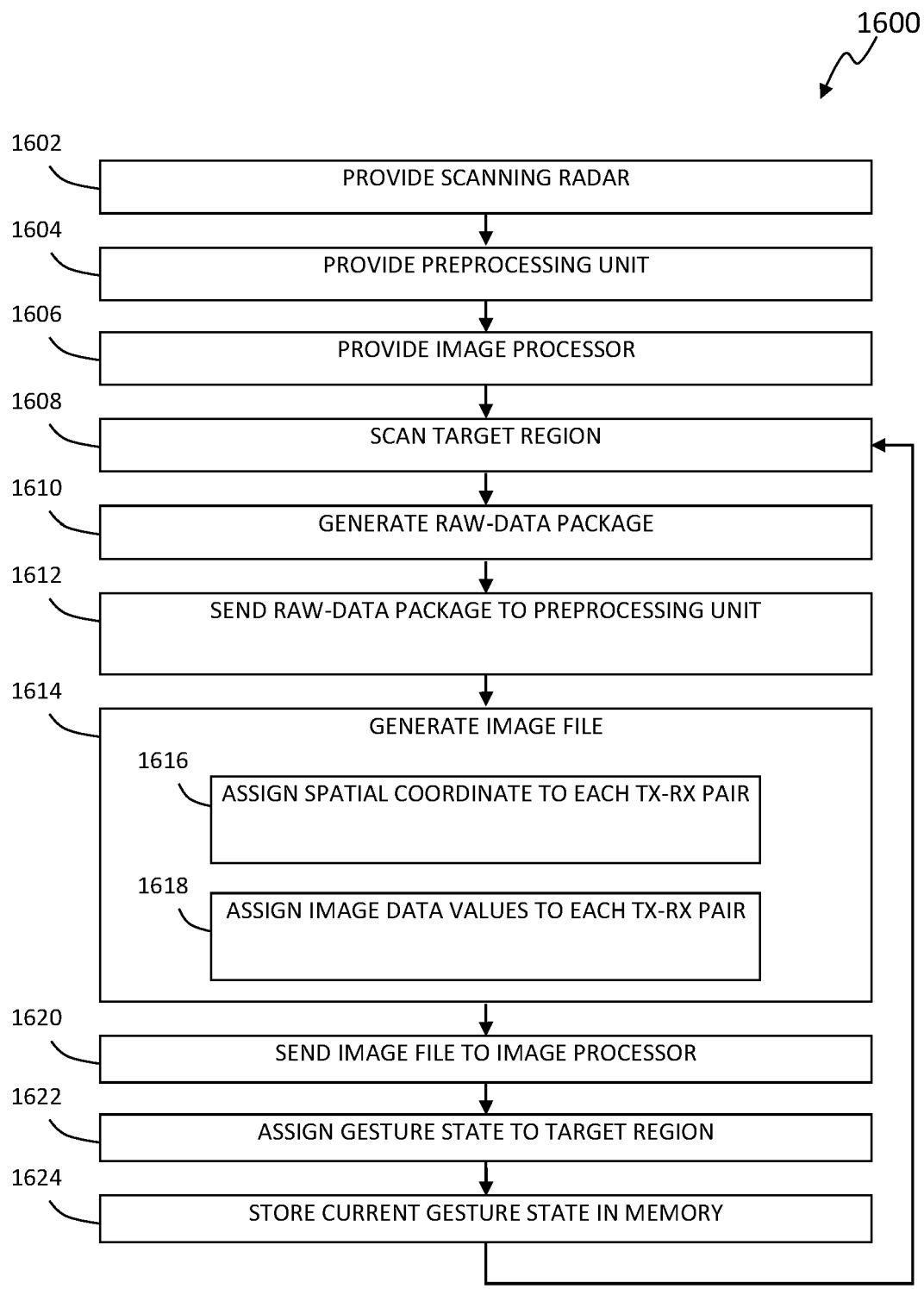
FIG. 16 is a flowchart representing selected steps in a method for gesture recognition using a scanning radar.
Figure 20G:
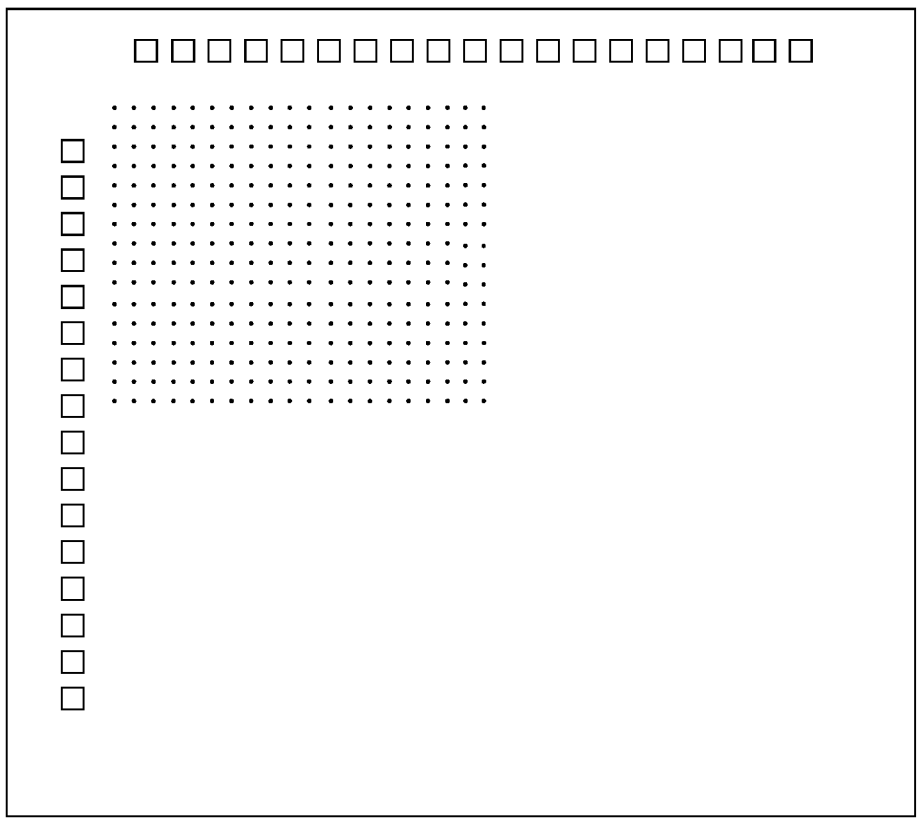
FIGS. 20A-G schematically illustrate a possible method for assigning spatial coordinates to each TX-RX pair.
Figure 20B:
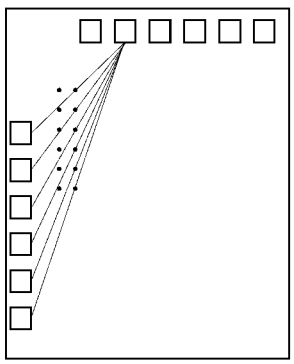
Figure 20D:
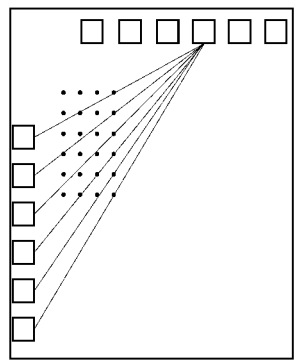
Figure 20F:
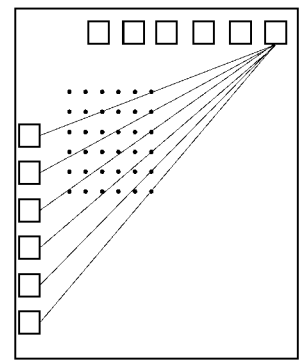
Figure 20A:
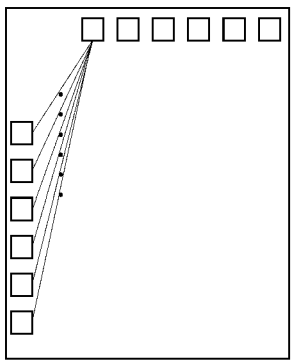
Figure 20C:
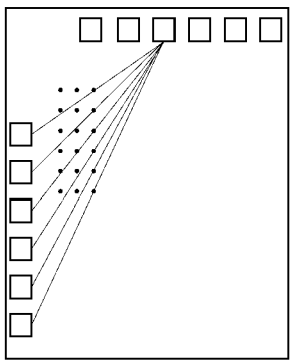
Figure 20E:
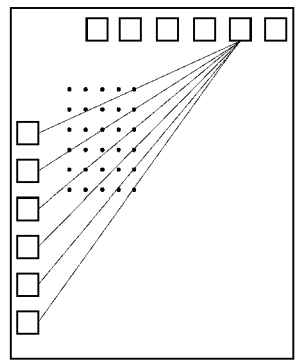
Figures 21A, 21B, 21C:
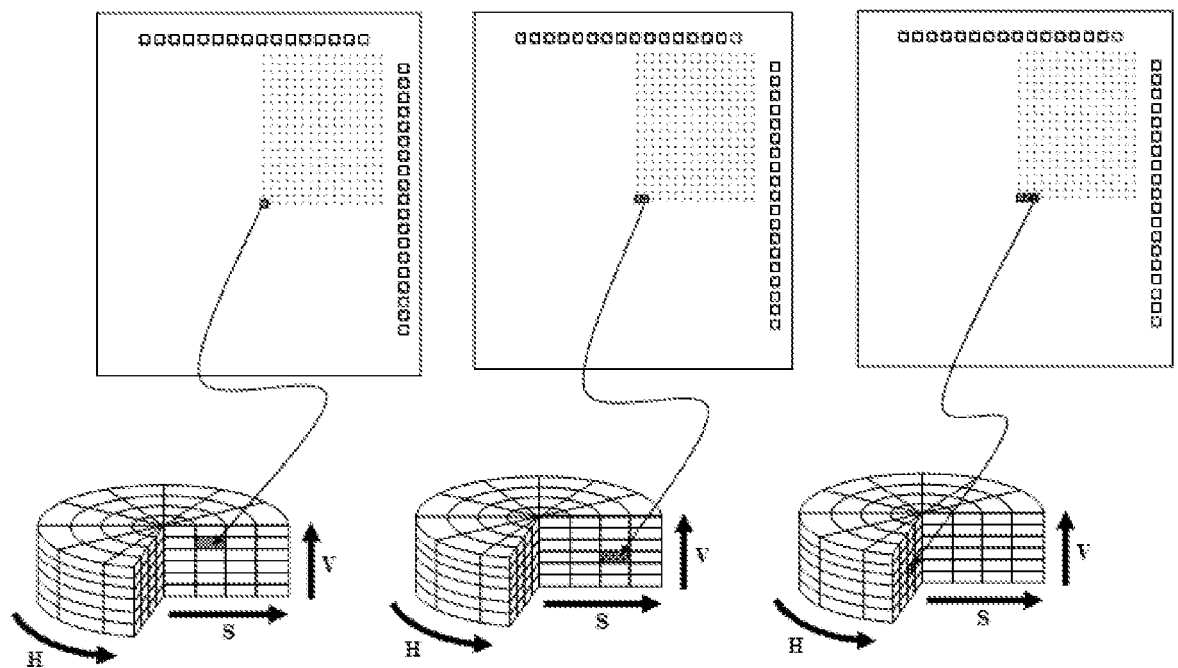
FIGS. 21A-D schematically illustrate a possible method for assigning image data values to each TX-RX pair.
Figure 21D:
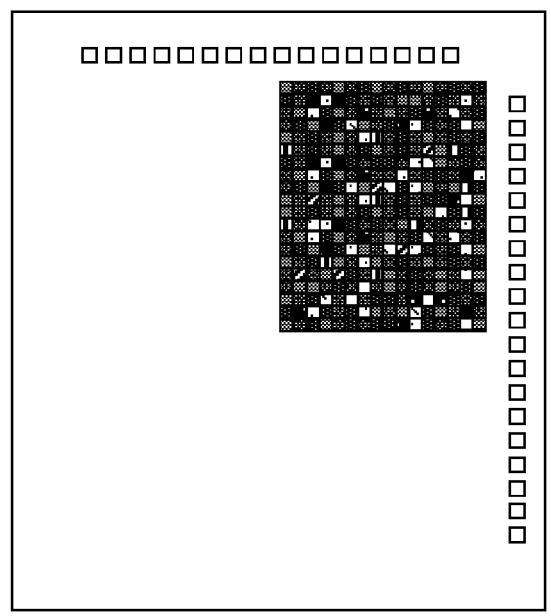

Reference is now made to the flowchart 1600 of FIG. 16 which represents selected steps in a method for gesture recognition using a scanning radar.

The method includes providing a scanning radar 1602, providing a preprocessing unit 1604 and providing an image processor 1606.

By way of example the scanning radar may be a linear array of transmitter antennas and a linear array of receiver antennas such as described hereinbelow.

The preprocessing unit may include various elements such as a communication unit operable to receive a raw-data package from the scanning radar and a memory element operable to store a received data package, and a processor operable to execute data-conversion protocols thereby generating an image data file.

Typically, the image processor may include a communication unit operable to receive the image data file from the preprocessor as well as a pattern recognition unit operable to detect patterns within the image data file.

The radar may scan a target region 1608 by transmitting and receiving scanning radiation over the target region. The scan may generate at least one raw-data package 1610 for example an associated phase value and an associated amplitude value for each transmitter-receiver pair of antennas.

The radar sends the raw-data package to the preprocessing unit 1612. The preprocessing unit, upon receiving the raw-data package may execute the data-conversion protocol such as a conversion function operating upon an input set of amplitude values and phase values associated with transmitter-receiver pairs. The data conversion protocol may thereby generate an image file output 1614.

Typically, the image file may be generated by the preprocessing unit assigning to each transmitter-receiver pair of antennas at least one spatial coordinate 1616 and a set of image data values based upon at least the associated phase value and the associated amplitude value 1618.

The preprocessing unit may then send the image file to the image processor 1620. The image processor may execute image recognition operations upon the image file data thereby generating gesture states for the target region 1622.

The current gesture state may be stored in a memory 1624. A series of such gesture states may be accumulated over time such that a history of gesture states may indicate a particular gesture made within the target region. Optionally an output notification may only be triggered in the event of the gesture state changing.

Various image recognition methods may be used to process image data to select gestures, possibly from a group of candidate gestures such as a no hand present state, a closed-hand state, a one-finger state, a two-finger state, a three-finger state, a four-finger state, a five-finger state and the like as well as combinations thereof. Gestures may be selected from still other possible candidate gestures as required. Optionally an output notification may only be triggered in the event of the gesture state changing.

Reference is now made to the block diagram of FIG. 17 which represents selected elements of a system for gesture recognition using a scanning radar. The system includes a scanning radar 1702, a pre-processor 1704, an image processor 1706 and an output unit 1708.

The scanning radar 1702 typically includes a first linear array of transmitter antennas and a second linear array of receiver antennas. Where appropriate, the first linear array and the second linear array may be orientated orthogonally such that the receiver arrays form a line perpendicular to the transmitter arrays.

The preprocessing unit 1704 typically includes a preprocessing communication unit operable to receive a raw-data package from the radar 1702 and a memory element operable to store a received raw-data package. The preprocessor 1704 may also include a central processing unit (CPU) operable to execute a data-conversion protocol generating an image data file.

The image processor 1706 may include a communication unit operable to receive at image data files from the preprocessing unit 1704 and a pattern recognition unit operable to detect patterns within the image data file.

Referring now to FIG. 18, data may be transferred between the antenna array radar 1702, the pre-processing unit 1704 and the image processor 1706 in packets. For example, a radar having n transmitter antennas and m receiver antennas may pass a total number of n×m pairs of amplitude and phase values for each scanning frequency. The n×m pairs correspond to amplitude and phase values of signals received by each receiver antenna for each transmitter antenna.

By way of example, one particular scanning radar may have, say, 16 transmitter antennas and 20 receiver antennas which are configured to scan at five individual frequencies between 60 GHz and 66 GHz. Such a scanner will produce a raw data package consisting of a total of 1600 pairs of amplitude and phase values which may be divided into 5 sets of 320 pairs sampled at each frequency.

The pre-processing unit 1704 receives the raw-data package and processes the data to produce image data files.

It is noted that image files generally assign three or four parameters to every spatial coordinate. Accordingly, by assigning a spatial coordinate to each RX-TX pair and encoding the phase and amplitude values using color encoding, an image file may be produced which may be passed to an image recognition processor for analysis.

Image files may use various color encoding systems such as RGB, CMY, YUV, HSV, HSL, HCL and the like. It is particularly noted that hue-saturation-value (HSV) or hue-saturation-lightness (HSL) color models encode the HUE value of the color cyclically. Accordingly, such coding systems may be particularly suited for coding raw-data packages including phase values. Phase values are by their nature cyclical, ranging from 0-2π but where adding 2π to any phase value does not alter the resulting phase. Similarly the cyclic nature of the HUE value is such that while it ranges from 0-1, adding 1 to any HUE value results in the same hue.

Accordingly, phase values φ may be normalized, say by dividing the raw-data phase value or an RX-TX pair by 2π to produce a value for the HUE parameter of the corresponding spatial coordinate. Alternatively, a HUE parameter may be selected by determining an x-coordinate and a y-coordinate on the unit circle (cos φ, sin φ) in color space, where φ is the phase.

Thus, the pre-processing unit 1704 typically produces an image file encoded using HSV or HSL values such that the HUE parameter is used to represent the phase in the raw data and one of the other linear parameters, say the SATURATON, VALUE or LIGHTNESS, is used to represent the amplitude value in the raw data.

Accordingly, the amplitude value of the raw-data may be normalized, for example by dividing the value by determining a signal-to-noise ratio for the raw data and setting one of the linear parameter values according to the signal-to-noise ratio. For example, one of the linear parameter values maybe set to the ratio of the amplitude value in the raw data value and the signal-to-noise ratio.

It is noted that the three-parameter coding of color allows an additional value to be encoded in the image which may be used to encode a different characteristic as required, for example to encode a Doppler value for a particular raw-data pair.

In particular, regarding Doppler values, encoding a Doppler value may enable the use of machine or deep learning networks to compensate for microvibrations of the objects being monitored, such as physiological movements of the hands during a gesture. Furthermore, Doppler values may be used for classifying dynamic gestures.

In this manner image frames may be generated to represent the raw data produced during the scan, with each frame relating to a scan at a particular frequency. Bundles of such image frames may be transferred to the image processor 1706 to serve as input data for a gesture recognition process.

Referring now to FIGS. 19A-C which indicate various hand states which may be present in the target region proximate to a scanning radar. The detection range may be limited to the proximate region, for example up to 50 cm from the radar scanner although systems may be configured for larger ranges where required.

Referring now to FIGS. 20A-G, schematically illustrating a possible method for assigning spatial coordinates to each TX-RX pair, the preprocessing unit 1704 may assign spatial coordinates to each transmitter-receiver pair of antennas 1702 by: determining the geometrical midpoint between the transmitter of the transmitter-receiver pair; selecting a horizontal coordinate for the transmitter-receiver pair corresponding to the horizontal coordinate of the geometrical midpoint between the transmitter of the transmitter-receiver pair; and selecting a vertical coordinate for the transmitter-receiver pair corresponding to the vertical coordinate of the geometrical midpoint between the transmitter of the transmitter-receiver pair.

It is noted that because the radar 1702 is a multiple input and multiple output device (MIMO), the received signals represent a measurement of a reflected common wavefront. Therefore, a TX-RX center of phase arrangement such as described herein may improve the preservation of the spatial relationship between the radar signals.

Accordingly, each point may be assigned image data based upon an HSV color encoding scheme to build an image frame as illustrated in FIGS. 21A-D.

The invention is described herein in the context of processing sets of raw signals. Additional embodiment is applying the techniques of mapping signal data to image data after initial transformation. For example, the spatial-domain data arising from the transmit-receive antenna pairs and the corresponding virtual array may be transformed into direction-domain data, such as elevation-azimuth based data prior to mapping into image. Similarly, frequency domain data may be transformed into time-domain data prior to mapping. In all these cases, the transformed data is still a complex-valued data, in which, for example, the phase evolution is indicative of Doppler activity. In certain cases, the transformed data may better reveal the spatial structure of the scene and improve the performance of the machine learning techniques.

It is further noted that while the invention is described in the context of MIMO-radar setting, the mapping of complex-valued signals and signal sets onto color images for further processing by Machine Learning techniques, as described, may be applied to additional radar and non-radar problems.

It is appreciated that certain features of the invention, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the invention has been described in conjunction with specific embodiments thereof, it is evident that other alternatives, modifications, variations and equivalents will be apparent to those skilled in the art. Accordingly, it is intended to embrace all such alternatives, modifications, variations and equivalents that fall within the spirit of the invention and the broad scope of the appended claims. Additionally, the various embodiments set forth hereinabove are described in terms of exemplary block diagrams, flow charts and other illustrations. As will be apparent to those of ordinary skill in the art, the illustrated embodiments and their various alternatives may be implemented without confinement to the illustrated examples. For example, a block diagram and the accompanying description should not be construed as mandating a particular architecture, layout or configuration.

The invention claimed is:

1. An elevator monitoring system (500) for monitoring passengers using an elevator system, the elevator monitoring system comprising:
    at least one cabin-based radar monitor (524) configured and operable to monitor passengers within at least one elevator cabin;
    at least one waiting zone radar monitor (514) configured and operable to monitor passengers in a waiting zone;
    a processor (528) configured and operable to receive data from the at least one cabin-based radar monitor and the at least one waiting zone radar monitor, to analyze data received from the at least one cabin-based radar monitor and the at least one waiting zone radar monitor and to execute an elevator control function to control a stop schedule of the elevator system; and
    a health monitor configured and operable to measure at least one health parameter of each passenger within the at least one elevator cabin and the waiting zone, wherein the health monitor comprises at least one array of radio frequency transmitter antennas (708) and at least one array of radio frequency receiver antennas (710), wherein the at least one array of radio frequency transmitter antennas are connected to an oscillator and are configured and operable to transmit electromagnetic waves within the at least one elevator cabin and the waiting zone, and wherein the radio frequency receiver antennas are configured to receive the electromagnetic waves reflected back from objects within the at least one elevator cabin and the waiting zone.

2. The elevator monitoring system (500) of claim 1, wherein the elevator control function is operable to prevent movement of the at least one elevator cabin if the received data indicates that cabin passenger density is above a threshold value.

3. The elevator monitoring system (500) of claim 1, wherein the elevator control function is operable to prevent elevator doors closing if the received data indicates that cabin passenger density is above a threshold value.

4. The elevator monitoring system (500) of claim 1, wherein the elevator control function is operable to prevent elevator doors closing if the received data indicates that a passenger is approaching the at least one elevator cabin.

5. The elevator monitoring system (500) of claim 1, further comprising a security scanner configured to generate security passes for passengers, and wherein the elevator control function is operable to prevent elevator doors from closing if the received data indicates that a number of passengers within the at least one elevator cabin is more than the security passes provided.

6. A method for controlling a stop schedule of an elevator system, the method comprising:
    providing (800) an elevator monitoring system for monitoring passengers using the elevator system, wherein the elevator monitoring system is configured for:
    providing (802) at least one cabin-based radar monitor configured and operable to monitor passengers within at least one elevator cabin;
    providing (804) at least one waiting zone radar monitor configured and operable to monitor passengers in a waiting zone; and providing (806) a processor configured and operable to receive (810) data from the at least one cabin-based radar monitor and the at least one waiting zone radar monitor, to analyze the data received from the at least one cabin-based radar monitor and the at least one waiting zone radar monitor and to execute (816) an elevator control function to control (818) the elevator system;

the method further comprising:

providing a health monitor configured and operable to measure at least one health parameter of each passenger within the at least one elevator cabin and the waiting zone, wherein the at least one health parameter includes one or more of the following: heart rate, heart variability, respiratory rate, gait sleep scores, posture, temperature, weight and blood pressure of the passenger;

wherein providing the health monitor further comprising providing at least one array of radio frequency transmitter antennas and at least one array of radio frequency receiver antennas, wherein the at least one array of radio frequency transmitter antennas are connected to an oscillator and are configured and operable to transmit electromagnetic waves within the at least one elevator cabin and the waiting zone, and wherein the radio frequency receiver antennas are configured to receive the electromagnetic waves reflected back from objects within the at least one elevator cabin and the waiting zone.

7. The method of claim 6, further comprising preventing movement of the at least one elevator cabin if the received data indicates that at least one elevator cabin passenger density is above a threshold value.

8. The method of claim 6, further comprising preventing elevator doors closing if the received data indicates that a passenger is approaching the at least one elevator cabin.

9. The method of claim 6 further comprising providing a security scanner configured to generate security passes for passengers, and wherein executing the elevator control function comprises preventing elevator doors from closing if the received data indicates that the number of passengers within the at least one elevator cabin is more than the security passes provided.

\* \* \* \* \*